US007405275B2

(12) United States Patent
Qin et al.

(10) Patent No.: US 7,405,275 B2
(45) Date of Patent: Jul. 29, 2008

(54) ANTIBODIES WHICH BIND HUMAN CXCR3

(75) Inventors: Shixin Qin, Lexington, MA (US); Nasim Kassam, Waltham, MA (US); Walter Newman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 99 days.

(21) Appl. No.: 10/949,135

(22) Filed: Sep. 24, 2004

(65) Prior Publication Data

US 2005/0112119 A1    May 26, 2005

Related U.S. Application Data

(60) Provisional application No. 60/505,697, filed on Sep. 24, 2003.

(51) Int. Cl.
C07K 16/00 (2006.01)
C12P 21/08 (2006.01)
A61K 39/395 (2006.01)
C12N 5/06 (2006.01)

(52) U.S. Cl. .............. 530/387.1; 530/387.3; 530/388.1; 530/388.15; 530/388.22; 424/130.1; 424/132.1; 424/133.1; 424/143.1; 435/326; 435/328; 435/334

(58) Field of Classification Search ................. None
See application file for complete search history.

(56) References Cited

U.S. PATENT DOCUMENTS

| 6,184,358 | B1 | 2/2001 | Loetscher et al. |
| 6,255,455 | B1 | 7/2001 | Siegel |
| 6,730,300 | B2 | 5/2004 | Leung et al. |
| 2002/0193571 | A1 | 12/2002 | Carter et al. |
| 2003/0040605 | A1 | 2/2003 | Siegel |

FOREIGN PATENT DOCUMENTS

| EP | 1264885 A1 | 12/2002 |
| WO | WO 00/29583 A2 | 5/2000 |
| WO | WO 01/62932 A1 | 8/2001 |
| WO | WO 02/060954 A1 | 8/2002 |
| WO | WO 02/084277 A1 | 10/2002 |
| WO | WO 02/086085 A2 | 10/2002 |
| WO | WO 02/102972 A2 | 12/2002 |

OTHER PUBLICATIONS

Li et al. Biochemistry 2000. 39:6296-6309.*
Padlan et al. FASEB J. 1995. 9:133-139.*
Brummell et al. Biochemistry. 1993. 32;4:1180-1187.*
Wang, X., et al., "Immunoglobulin heavy chain variable region [*Homo sapiens*]" May 8, 2001 (sequence) GenPept [online] Bethesda, MD, USA: National Center for Biotechnology Information [retrieved on Nov. 14, 2006] GenPept Accession No. AAD53840.

Nikitin, E. A., "Immunoglobuilin heavy chain variable region [*Homo sapiens*]" Nov. 30, 2001 (sequence) GenPept [online] Bethesda, MD, USA: National Center for Biotechnology Information [retrieved on Nov. 14, 2006] GenPept Accession No. CAC88733.
Johnson, T. A., "IgM heavy chain VH1 region precursor [*Homo sapiens*]" Aug. 27, 1997 (sequence) GenPept [online] Bethesda, MD, USA: National Center for Biotechnology Information [retrieved on Nov. 14, 2006] GenPept Accession No. AAC51708.
Johnson T. A., "IgM heavy chain VH1 region precursor [*Homo sapiens*]" Aug. 27, 1997 (sequence) GenPept [online] Bethesda, MD, USA: National Center for Biotechnology Information [retrieved on Nov. 14, 2006] GenPept Accession No. AAC51699.
Kurosawa, Y., "Immunoglobulin heavy chain VHDJ region [*Homo sapiens*]" Jul. 2, 2002 (sequence) GenPept [online] Bethesda, MD, USA: National Center for Biotechnology Information [retrieved on Nov. 14, 2006] GenPept Accession No. BAC02190.
Wang, X., et al., "Immunoglobulin heavy chain variable region [*Homo sapiens*]" May 8, 2001 (sequence) GenPept [online] Bethesda, MD, USA: National Center for Biotechnology Information [retrieved on Nov. 14, 2006] GenPept Accession No. AAC18298.
Kurosawa, Y., "Immunoglobulin heavy chain VHDJ region [*Homo sapiens*]" Jul. 2, 2002 (sequence) GenPept [online] Bethesda, MD, USA: National Center for Biotechnology Information [retrieved on Nov. 14, 2006] GenPept Accession No. BAC02366.
Nikitin, E. A., "Immunoglobulin heavy chain variable region [*Homo sapiens*]" Nov. 30, 2001 (sequence) GenPept [online] Bethesda, MD, USA: National Center for Biotechnology Information [retrieved on Nov. 14, 2006] GenPept Accession No. CAC88742.
Qin, Shixin, et al., "The chemokine receptors CXCR3 and CCR5 mark subsets of T cells associated with certain inflammatory reactions," *Journal of Clinical Investigation*, vol. 101, No. 4 (Feb. 1998) pp. 746-754.
Paul, S., et al., "Recombinant single chain Fv antibody [synthetic construct]" Feb. 17, 2001 (sequence) GenPept [online] Bethesda, MD, USA: National Center for Biotechnology Information [retrieved on Nov. 14, 2006] GenPept Accession No. AAK09209.
Deshpande, R. V., et al., "Unnamed protein product [*Homo sapiens*]," Sep. 11, 2001 (sequence) GenPept [online] Bethesda, MD, USA: National Center for Biotechnology Information [retrieved on Nov. 14, 2006] GenPept Accession No. CAC69719.
Davidson, A., et al., "Human Ig rearranged kappa-chain mRNA V1-J2 region, 5' end" Apr. 27, 1993 (sequence) GenBank [online] Bethesda, MD, USA: National Center for Biotechnology Information [retrieved on Nov. 14, 2006] GenBank Accession No. M33060.

(Continued)

*Primary Examiner*—Maher M. Haddad
*Assistant Examiner*—Chun Dahle

(57) ABSTRACT

Antibodies and antigen-binding fragments of antibodies that bind human CXCR3 are disclosed. In preferred embodiments, the antibodies are human. Nucleic acids and vectors encoding the antibodies or portions thereof, recombinant cells that contain the nucleic acids, and compositions comprising the antibodies or antigen-binding fragments are also disclosed. The invention also provides therapeutic and diagnostic methods which employ the antibodies and antigen-binding fragments.

17 Claims, 4 Drawing Sheets

OTHER PUBLICATIONS

Zachau, H. G., "*H. sapiens* mRNA for rearranged Ig kappa light chain variable region (I.45)" Jan. 31, 1994 (sequence) GenBank [online] Bethesda, MD, USA: National Center for Biotechnology Information [retrieved on Nov. 14, 2006] GenBank Accession No. X72427.

Sims, G. P., "Anti-acetylcholine receptor immunoglobulin kappa light chain variable region [*Homo sapiens*]" Nov. 4, 2002 (sequence) GenPept [online] Bethesda, MD, USA: National Center for Biotechnology Information [retrieved on Nov. 14, 2006] GenPept Accession No. AAK61521.

Chazenbalk, G. D., et al., "Immunoglobulin kappa-chain [*Homo sapiens*]" Feb. 12, 2001 (sequence) GenPept [online] Bethesda, MD, USA: National Center for Biotechnology Information [retrieved on Nov. 14, 2006] GenPept Accession No. AAA02605.

Kurosawa, Y., "Immunoglobulin kappa light chain VLJ region [*Homo sapiens*]" Jul. 2, 2002 (sequence) GenPept [online] Bethesda, MD, USA: National Center for Biotechnology Information [retrieved on Nov. 14, 2006] GenPept Accession No. BAC01726.

Zachau, H. G., "Ig kappa light chain (VJ) [*Homo sapiens*]" Jan. 31, 1994 (sequence) GenPept [online] Bethesda, MD, USA: National Center for Biotechnology Information [retrieved on Nov. 14, 2006] GenPept Accession No. CAA51109.

Kurosawa, Y., "Immunoglobulin kappa light chain VLJ region [*Homo sapiens*]" Jul. 2, 2002 (sequence) GenPept [online] Bethesda, MD, USA: National Center for Biotechnology Information [retrieved on Nov. 14, 2006] GenPept Accession No. BAC01557.

Chiorazzi, N., "Immunoglobulin light chain variable region [*Homo sapiens*]" Apr. 27, 1995 (sequence) GenPept [online] Bethesda, MD, USA: National Center for Biotechnology Information [retrieved on Nov. 14, 2006] GenPept Accession No. CAA59082.

Tachibana, H., "Immunoglobulin kappa light chain [*Homo sapiens*]" Mar. 27, 2002 (sequence) GenPept [online] Bethesda, MD, USA: National Center for Biotechnology Information [retrieved on Nov. 14, 2006] GenPept Accession No. BAA97671.

Horn, M. P., "Light chain Fab fragment [*Homo sapiens*]" Jan. 8, 1997 (sequence) GenPept [online] Bethesda, MD, USA: National Center for Biotechnology Information [retrieved on Nov. 14, 2006] GenPept Accession No. CAA69342.

Chang, T. Y., et al., "Anti-Rh(D) antibody V kappa segment [synthetic construct]" Oct. 31, 2001 (sequence) GenPept [online] Bethesda, MD, USA: National Center for Biotechnology Information [retrieved on Nov. 14, 2006] GenPept Accession No. ACC13456.

Kurosawa, Y., "Immunoglobulin kappa light chain VLJ region [*Homo sapiens*]" Jul. 2, 2002 (sequence) GenPept [online] Bethesda, MD, USA: National Center for Biotechnology Information [retrieved on Nov. 14, 2006] GenPept Accession No. BAC01704.

Welschof, M., "Immunoglobulin kappa light chain variable region [*Homo sapiens*]" Oct. 19, 1995 (sequence) GenPept [online] Bethesda, MD, USA: National Center for Biotechnology Information [retrieved on Nov. 14, 2006] GenPept Accession No. CAA85587.

\* cited by examiner ial Application No. 60/505,697, filed Sep. 24, 2003, the contents of which are incorporated herein by this reference in its entirety.

BACKGROUND OF THE INVENTION

C-X-C chemokine receptor-3 (CXCR3) is expressed on certain leukocytes, such as activated T cells and NK cells. The CXCR3 receptor binds ligands, such as Interferon Gamma-inducible 10 kD Protein (IP-10), Monokine Induced by Gamma interferon (MIG; Mig), Interferon-inducible T-cell Alpha Chemoattractant (I-TAC) and B cell-attracting chemokine-1 (BCA-1). Certain forms of CXCR3 also bind platelet factor-4 (PF-4, Lasagni et al. (2003) *J. Exp. Med.* 197:1537-1549). The expression of some of the CXCR3 ligands (IP-10, MIG and I-TAC), is induced in tissues by inteferons or Tumor Necrosis Factor (TNF), potent mediators of inflammation (Farber, J. M. (1997) *J. Leukoc. Biol.* 61:246-257; Piali, et al. (1998) *Eur. J. Immunol.* 28:961-972; Cole et al. (1998) *J. Exp. Med.* 187:2009-2021). Because of these findings, it has been postulated that during inflammation, expression of ligands for CXCR3 is upregulated, resulting in recruitment of CXCR3+ lymphocytes into the inflamed tissue. The infiltrating CXCR3+ lymphocytes can contribute to adverse pathological effects of inflammation. Inhibiting the activities of CXCR3, therefore, can have beneficial anti-inflammatory effects. There is a need for therapeutic agents that inhibit CXCR3 function.

SUMMARY OF THE INVENTION

The invention relates to antibodies and antigen-binding fragments of antibodies, such as human monoclonal antibodies, which bind human CXCR3. In certain embodiments, the antibodies and antigen-binding fragments can also bind ligand-binding variants of human CXCR3 and/or fragments of human CXCR3. In one embodiment, the antibody or antigen-binding fragment thereof binds an extracellular loop of human CXCR3. In another embodiment, the antibody or antigen-binding fragment thereof inhibits the binding of a ligand (e.g., IP-10, MIG or I-TAC, or a CXCR3-binding variant or fragment of IP-10, MIG or I-TAC) to human CXCR3. In other embodiments, the antibody or antigen-binding fragment inhibits binding of at least 3 ligands, such as IP-10, MIG and I-TAC, to human CXCR3. In other embodiments, the antibody or antigen-binding fragment inhibits ligand-induced activity of CXCR3. For example, an antibody of the invention can inhibit CXCR3-mediated signal transduction, intracellular calcium (Ca++) release, more specifically the induction of a rapid and transient increase in the concentration of cytosolic free calcium $[Ca^{2+}]_i$ (calcium flux), chemotaxis, cell differentiation or cell proliferation that is induced upon ligand binding. In particular embodiments, the antibody or antigen-binding fragment competitively inhibits binding of human mAb 5H7 or human mAb 7H5 to CXCR3, or has the epitopic specificity of human mAb 5H7 or human mAb 7H5.

In some embodiments, the antibody or antigen-binding fragment comprises one, two or three heavy chain complementarity determining regions (HCDR1, HCDR2 and/or HCDR3) having the amino acid sequences of heavy chain CDR1, CDR2 and CDR3 of human mAb 5H7. In certain embodiments, one amino acid residue in the heavy chain CDR1, one or two amino acid residues in the heavy chain CDR2, and/or one, two or three amino acid residues in CDR3 can be conservatively substituted as described herein. The antibody or antigen-binding fragment can further comprise one, two or three light chain complementarity determining regions (LCDR1, LCDR2 and/or LCDR3) having the amino acid sequences of light chain CDR1, CDR2 and CDR3 of human mAb 5H7. In certain embodiments, one or two amino acid residues in the light chain CDR1, one amino acid residue in the light chain CDR2 and/or one or two amino acid residues in the light chain CDR3 can be conservatively substituted. Preferably, the antibody or antigen-binding fragment comprises the three heavy chain CDRs and the three light chain CDRs of human mAb 5H7. In more particular embodiments, the antibody or antigen-binding fragment comprises the heavy chain variable region of human mAb 5H7 (5H7 VH, SEQ ID NO: 2) and the light chain variable region of human mAb 5H7 (5H7 VK, SEQ ID NO:10).

In other embodiments, the antibody or antigen-binding fragment thereof comprises one, two or three heavy chain complementarity determining regions (HCDR1, HCDR2 and/or HCDR3) having the amino acid sequences of the heavy chain CDR1, CDR2, and CDR3 of human mAb 7H5. In certain embodiments, one amino acid residue in the heavy chain CDR1, one or two amino acid residues in the heavy chain CDR2 and/or one, two or three amino acid residues in the heavy chain CDR3 can be conservatively substituted. The antibody or antigen-binding fragment can further comprise one, two or three light chain complementarity determining regions (LCDR1, LCDR2 and/or LCDR3) having the amino acid sequences of the light chain CDR1, CDR2, and CDR3 of human mAb 7H5. In certain embodiments, one or two amino acid residues in the light chain CDR1, one amino acid residue in the light chain CDR2 and/or one or two amino acid residues in the light chain CDR3 can be conservatively substituted. Preferably, the antibody or antigen-binding fragment comprises the three heavy chain CDRs and the three light chain CDRs of human mAb 7H5. In more particular embodiments, the antibody or antigen-binding fragment comprises the heavy chain variable region of human mAb 7H5 (7H5 VH, SEQ ID NO:18) and the light chain variable region of human mAb 7H5 (7H5 VK, SEQ ID NO:26).

Preferred antibodies and antigen-binding fragments that bind human CXCR3 include human antibodies, chimeric antibodies, humanized antibodies, single chain antibodies and antigen-binding fragments of the foregoing, such as Fab fragments, Fab' fragments, F(ab')₂ fragments and Fv fragments. Particularly preferred antibodies and antigen-binding fragments are human. In specific embodiments, the invention is human mAb 5H7 or an antigen-binding fragment of human mAb 5H7 or human mAb 7H5 or an antigen-binding fragment of human mAb 7H5.

The invention also relates to the heavy chains, light chains and antigen-binding portions of the heavy chains and light chains of the antibodies described herein. The invention also relates to fusion proteins comprising an antibody or portion thereof (e.g., heavy chain, light chain, variable region) of the invention and a non-immunoglobulin moiety. The invention also relates to immunoconjugates comprising an antibody or antigen-binding fragment of the invention and a second moiety, such as a toxin (e.g., cytotoxin, cytotoxic agent), a therapeutic agent (e.g., a chemotherapeutic agent, an antimetabolite, an alkylating agent, an anthracycline, an antibiotic, an anti-mitotic agent, a biological response modifier (e.g., a cytokine, a growth factor (e.g., a neurotrophic factor)), a plasminogen activator, a radionuclide (e.g., a radioactive ion)), an enzyme or a detectable label, e.g., a radionuclide.

The invention also relates to isolated and/or recombinant nucleic acids encoding the antibodies, antigen-binding fragments, heavy chains, light chains and portions of the heavy chains and light chains of the antibodies described herein, or fusion proteins and to expression constructs or vectors comprising same. The invention also relates to an expression construct comprising a recombinant nucleic acid molecule that encodes a heavy chain or an antigen-binding portion thereof, and to an expression construct comprising a recombinant nucleic acid molecule that encodes a light chain or an antigen-binding portion thereof. The invention also relates to a host cell that comprises a nucleic acid of the invention. The invention also relates to an isolated cell which produces a heavy chain or an antigen-binding portion thereof, a light chain or an antigen-binding portion thereof. In specific embodiments, the invention is hybridoma 5H7 or hybridoma 7H5.

The invention also relates to a composition comprising an antibody or antigen-binding fragment thereof, e.g., a monoclonal antibody (e.g. a human monoclonal antibody or antigen-binding fragment thereof, a heavy chain or antigen-binding portion thereof, a light chain or antigen-binding portion thereof, a chimeric antibody or antigen-binding fragment thereof), or an immuno-conjugate of an antibody described herein and a physiologically acceptable carrier. In specific embodiments, the composition comprises human monoclonal antibody 5H7 and/or human monoclonal antibody 7H5 and a physiologically acceptable carrier.

The invention also relates to a method of treating a subject having an inflammatory disease or disorder comprising administering to said subject an effective amount of an antibody or antigen-binding fragment of the invention. In particular embodiments, the subject is a human. In other particular embodiments, the subject has an inflammatory bowel disease, such as ulcerative colitis or Crohn's disease, an autoimmune disease, such as rheumatoid arthritis or multiple sclerosis.

The invention further relates to an antibody, antigen-binding fragment of an antibody (including antigen-binding fragments), immunoglobulin chain (including antigen-binding portions), fusion protein or immuno-conjugate as described herein for use in therapy (including prophylaxis) or diagnosis, and to the use of an antibody, antigen-binding fragment of an antibody, fusion protein or immuno-conjugate of the invention for the manufacture of a medicament for the treatment of a particular disease or condition as described herein. For example, the disease or condition can be a disease or condition mediated by a cell expressing CXCR3 (e.g., a T helper-1 cell, an eosinophil), an inflammatory disease (e.g., inflammatory bowel disease (e.g., ulcerative colitis, Crohn's disease)), an autoimmune disease (e.g., rheumatoid arthritis, multiple sclerosis, Graves' disease, diabetes), cancer (e.g., a lymphoproliferative disease), or an inflammatory disease precipitated by foreign matter (e.g., graft rejection, response to bacterial or viral infection), a respiratory inflammatory disease (e.g. chronic obstructive pulmonary disease)).

DETAILED DESCRIPTION OF THE INVENTION

Figure 1:
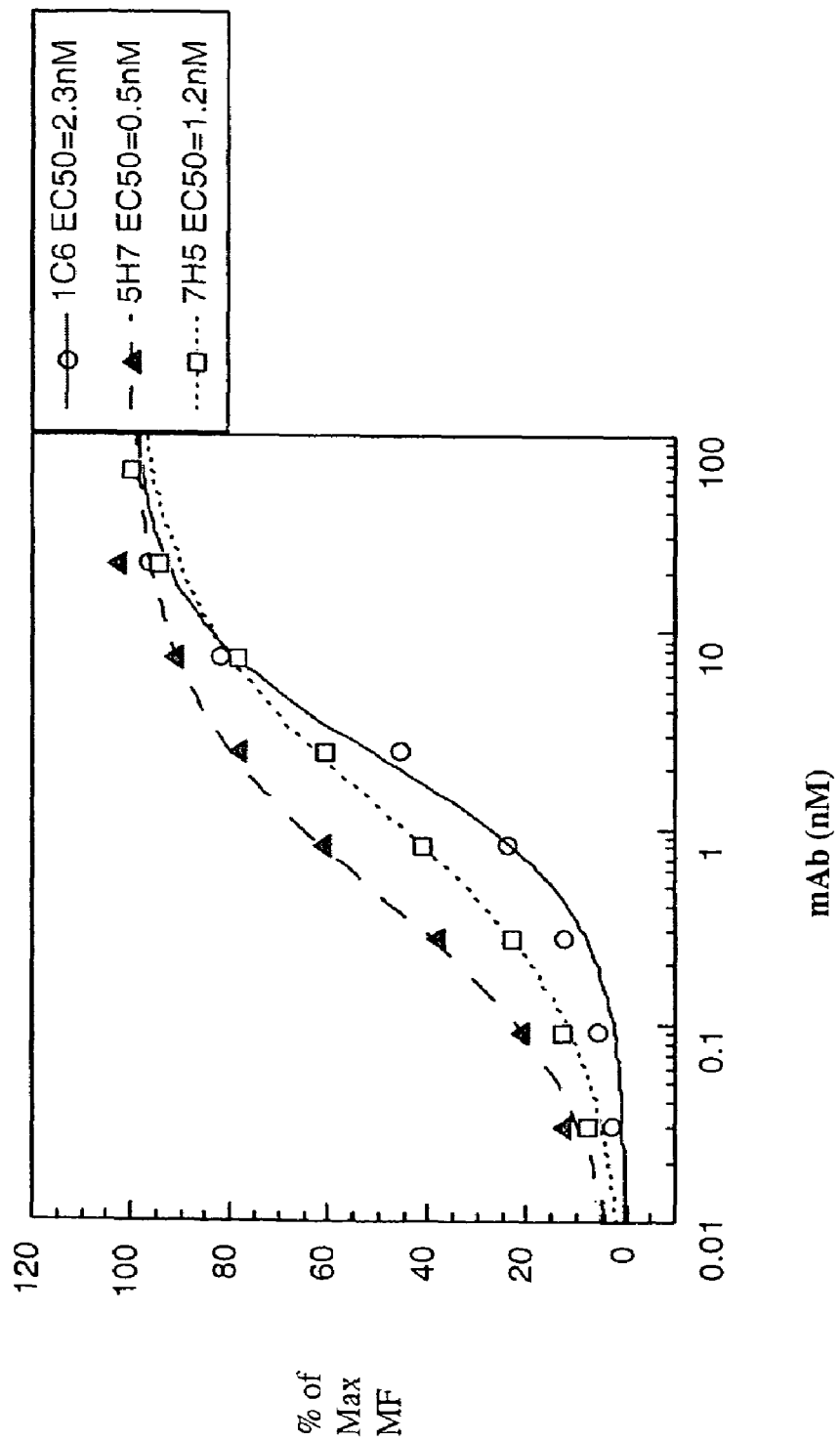
FIG. 1 is a graph showing the mean fluorescence (MF) intensity displayed by the binding of human monoclonal antibody (mAb) 5H7, human monoclonal antibody 7H5 or murine monoclonal antibody 1C6 to CXCR3 transfectants. The 100% value of mean fluorescence intensity, from which the EC50 was calculated, is the intensity of binding by 10 μg/ml of each antibody. The EC50 values are 0.5 nM, 1.2 nM and 2.3 nM for human mAb 5H7, human mAb 7H5 and murine mAb 1C6, respectively.

As used herein, the term "functionally rearranged" refers to a segment of DNA from an immunoglobulin locus which has undergone V(D)J recombination, with or without insertion or deletion of nucleotide(s) (e.g., N nucleotides, P nucleotides) and/or somatic mutation, thereby producing an immunoglobulin gene which encodes an immunoglobulin variable region or immunoglobulin chain (e.g., heavy chain, light chain). A functionally rearranged immunoglobulin gene can be directly or indirectly identified using suitable methods, such as, for example, nucleotide sequencing, hybridization (e.g., Southern blotting, Northern blotting) using probes which can anneal to coding joints between gene segments (e.g., VH, VL, D, JH, JL) or enzymatic amplification of immunoglobulin genes (e.g., polymerase chain reaction) with primers which can anneal to coding joints between gene segments. Whether a cell produces an antibody comprising a particular variable region or a variable region comprising a particular sequence (e.g., a CDR sequence) can also be determined using suitable methods. In one example, mRNA can be isolated from an antibody producing cell (e.g., a hybridoma) and used to produce cDNA. The cDNA can be cloned and sequenced or can be amplified (e.g., by polymerase chain reaction) using a first primer which anneals specifically to a portion of the variable region of interest (e.g., CDR, coding joint) and a second primer which anneals specifically to non-variable region sequences (e.g., $C_H1$, $C_L$).

As used herein, the phrase "of human origin" refers to antibodies, antigen-binding fragments of antibodies and portions or regions of antibodies (e.g., variable regions, complementarity determining regions (CDRs), framework regions (FRs), constant regions) having amino acid sequences that are encoded by nucleotide sequences derived from human (*Homo sapiens*) germ line immunoglobulin genes. For example, an antibody of human origin can be encoded by human germ line immunoglobulin genes that have been functionally rearranged to produce a functional gene that can be expressed to produce an antibody. As described herein, functionally rearranged genes that encode an antibody chain can include sequences that are not found in the germ line, such as N nucleotides and P nucleotides, and mutations that can occur as part of the processes that produce high-affinity antibodies (e.g., somatic mutation, affinity maturation, clonal selection). Functionally rearranged immunoglobulin genes of human origin, including those that include non-germ line sequences, can be generated via natural processes in a suitable in vivo expression system (e.g., a human, a human-antibody transgenic animal), artificially using any suitable methods (e.g., recombinant DNA technology, phage display) or any combination of natural and artificial processes. Antibodies, antigen-binding fragments of antibodies and portions or regions of antibodies of human origin can be produced, for example, by expression of a nucleic acid of non-human origin (e.g., a synthetic nucleic acid) that has the requisite nucleotide sequence.

An antibody, antigen-binding fragment of an antibody or a portion of an antibody (e.g., a framework region) "of human origin" can have an amino acid sequence that is encoded by a nucleic acid that has a nucleotide sequence that is a consensus of the nucleotide sequences of a number of naturally occurring human antibody genes or human germ line sequences, or have an amino acid sequence that is a consensus of the amino acid sequences of a number of naturally occurring human antibodies or amino acid sequences encoded in the human germ line. A number of human antibody consensus sequences are available, including consensus sequences for the different subgroups of human variable regions (see, Kabat, E. A., et al., *Sequences of Proteins of Immunological Interest*, Fifth Edition, U.S. Department of Health and Human Services, U.S. Government Printing Office (1991)). The Kabat database and its applications are freely available on line, e.g. via IgBLAST at the National Center for Biotechnology Information, Bethesda, Md. (also see, Johnson, G. and Wu, T. T., *Nucleic Acids Research* 29:205-206 (2001)).

As used herein, the phrase "human antibody" refers to an antibody or an antigen-binding fragment of an antibody in which the variable and constant regions (if present) have amino acid sequences that are encoded by nucleotide sequences derived from human (*Homo sapiens*) germline immunoglobulin genes. A "human antibody" can include sequences that are not encoded in the germline (e.g., due to N nucleotides, P nucleotides, and mutations that can occur as part of the processes that produce high-affinity antibodies such as, somatic mutation, affinity maturation, clonal selection) that occur as a result of biological processes in a suitable in vivo expression system (e.g., a human, a human-antibody transgenic animal). Antibodies, antigen-binding fragments of antibodies and portions or regions of human antibodies can be produced, for example, by expression of a nucleic acid of non-human origin (e.g., a synthetic nucleic acid) that has the requisite nucleotide sequence.

As used herein, the phrase "CDR-grafted" antibody refers to an antibody or an antigen-binding fragment of an antibody which comprises a CDR that is not naturally associated with the framework regions of the antibody or antigen-binding fragment. Generally the CDR is from an antibody from a first species and the framework regions and constant regions (if present) are from an antibody from a different species. The CDR-grafted antibody can be a "humanized antibody."

As used herein, "humanized antibody" refers to an antibody or antigen-binding fragment thereof comprising a CDR that is not of human origin and framework and/or constant regions that are of human origin. For example, a humanized antibody can comprise a CDR derived from an antibody of nonhuman origin (e.g., natural antibody such as a murine (e.g., mouse, rat) antibody, artificial antibody) that binds a human CXCR3, and framework and constant regions (if present) of human origin (e.g., a human framework region, a human consensus framework region, a human constant region (e.g., CL, CH1, hinge, CH2, CH3, CH4)). CDR-grafted single chain antibodies containing a CDR of non-human origin and framework and constant regions (if present) of human origin (e.g., CDR-grafted scFV) are also encompassed by the term humanized antibody.

As used herein, the term "chimeric antibody" refers to an antibody or antigen-binding fragment thereof comprising a variable region from an antibody from a first species and a constant region from an antibody from a different species. None of the portions which comprise a chimeric antibody needs to be of human origin. For example, a chimeric antibody can comprise a variable region from a rodent (e.g., mouse) antibody and a constant region of a non-human primate antibody (e.g., a chimpanzee constant region).

The antibody of the invention can be a single chain antibody (e.g., a single chain Fv (scFv)) and can include a linker moiety (e.g., a linker peptide) not found in native antibodies. For example, a scFv can comprise a linker peptide, such as two to about twenty glycine residues or other suitable linker, which connects a heavy chain variable region to a light chain variable region. For the purposes of the invention, the presence of such a linker does not affect the status of the single chain antibody as being "of human origin" or "human." For example, a human scFv can comprise a human heavy chain variable region and a human light chain variable region which are connected through a suitable peptide linker.

As used herein, "conservative amino acid substitution" refers to the replacement of one amino acid by another within the following groups: Ala, Val, Leu, and Ile; Ser and Thr; Asp and Glu; Asn and Gin; Lys and Arg; Phe and Tyr.

As used herein, a "CXCR3 protein" or "human CXCR3" refers to naturally occurring or endogenous human CXCR3 proteins and to proteins having an amino acid sequence which is the same as that of a naturally occurring or endogenous human CXCR3 protein (e.g., recombinant proteins). Accordingly, as defined herein, "CXCR3 protein" or "human CXCR3" includes mature protein, polymorphic or allelic variants, and other isoforms of human CXCR3 (e.g., produced by alternative splicing or other cellular processes), and modified or unmodified forms of the foregoing (e.g., glycosylated, unglycosylated, phosphorylated or unphosphorylated CXCR3 proteins). Naturally occurring or endogenous human CXCR3 proteins include wild type proteins such as mature CXCR3, polymorphic or allelic variants and other isoforms that occur naturally in humans. A nucleotide sequence encoding a full length human (*Homo sapiens*) CXCR3, used in the studies described herein is disclosed as "SEQ ID NO:1" in U.S. Pat. No. 6,184,358 B1, the contents of which are incorporated herein by reference in their entirety. This sequence is presented herein as SEQ ID NO: 33. The sequence of a human CXCR3 also is available in GenBank under accession number NM_001504. The entire teachings of GenBank Accession Number NM_001504 also are incorporated herein by reference. The nucleotide sequence of SEQ ID NO:33 has an open-reading frame from nucleotides 69-1175 (including stop codon). The amino acid sequence of a human CXCR3 encoded by SEQ ID NO: 33 is presented as SEQ ID NO: 34 ("SEQ ID NO:2" of U.S. Pat. No. 6,184,358 B1).

Human CXCR3 is a G protein-coupled receptor with an N-terminal extracellular region, seven transmembrane domains, three intracellular loops, three extracellular loops and a C-terminal cytoplasmic region. Ligand-binding variants of human CXCR3 can comprise an N-terminal extracellular region, at least one, two, three, four, five, six, preferably seven transmembrane domains, at least one, two, preferably three intracellular loops, at least one, two, preferably three extracellular loops and/or a C-terminal cytoplasmic region. The N-terminal extracellular region of human CXCR3 is located at about amino acid residues 1-58 of SEQ ID NO: 34, can be important for ligand binding and can include the epitope recognized by murine monoclonal antibody 1C6 previously described in U.S. Pat. No. 6,184,358 B1 and Qin et al. (1998) *J. Clin. Invest.* 101:746-754. The transmembrane domains are located at about amino acid residues 59-79, 91-111, 127-147, 170-190, 224-244, 257-277 and 302-322 of SEQ ID NO: 34. The extracellular loops of human CXCR3 are located at about amino acid residues 112-126, 191-223, and 278-301 of SEQ ID NO:34 and can be important for ligand binding. For example, the second extracellular loop (about residues 191-223 of SEQ ID NO:34) has been shown to be involved in ligand binding. The intracellular loops of human CXCR3 are located at about amino acid residues 80-90, 148-169, and 245-256 of SEQ ID NO:34 and, together with the C-terminal cytoplasmic region at about amino acid residues 323-368 of SEQ ID NO:34 can be important for function mediated by CXCR3 and induced by ligand binding, e.g. signal transduction, intracellular calcium release, chemotaxis, cell differentiation, cell proliferation and cell activation.

Allelic variants of human CXCR3 include both functional and non-functional proteins. Functional allelic variants are naturally occurring amino acid sequence variants of the CXCR3 protein that maintain the ability to bind a CXCR3 ligand and/or perform a CXCR3-mediated function. Non-functional allelic variants are naturally-occurring amino acid sequence variants of human CXCR3 protein that do not have the ability to bind a CXCR3 ligand and/or perform a CXCR3-mediated function. A number of allelic variants of human CXCR3 have been identified and these, amoung others, are encompassed by the term allelic variant. (See, e.g., Kato et al. (2000) *Genes Immun.* 1:330-337.)

Ligand-binding variants and fragments of human CXCR3 comprise at least one extracellular portion of human CXCR3. A ligand-binding variant or fragment of human CXCR3 can bind at least one ligand of CXCR3, such as IP-10, MIG, I-TAC, BCA-1 or a receptor-binding fragment of any of the foregoing. A ligand-binding variant or fragment of human CXCR3 can include a chemically synthesized peptide of CXCR3. A protein comprising an extracellular portion of human CXCR3 can be, for example, a deletion mutant. Such a deletion mutant can be expressed from a recombinant nucleic acid molecule encoding at least that extracellular portion of human CXCR3, for example. A library of nucleic acids encoding a population of ligand-binding CXCR3 fragments or variants can be expressed to produce a diverse population of CXCR3 variants for screening and/or subsequent selection of antibodies or antigen-binding fragments which bind CXCR3 variants.

For example, a protein comprising an extracellular portion of human CXCR3 can include at least a portion of the N-terminus of a human CXCR3, e.g., amino acid residues 1-37 or 1-58 of SEQ ID NO:34 and/or at least the second extracellular loop of a human CXCR3, e.g., amino acid residues 191-223 of SEQ ID NO:34. A protein comprising an extracellular portion of a human CXCR3 can be a fusion protein having an extracellular, e.g., ligand-binding, portion of a human CXCR3 fused to another molecule, e.g., a portion of another G protein-coupled receptor, a molecule having an entity which anchors the CXCR3 extracellular portion to a cell membrane, e.g., a heterologous transmembrane domain or a glycosylphosphatidylinositol membrane anchor, or a molecule designed to transduce a detectable signal when bound to a CXCR3 ligand.

"Human IP-10" includes immature and mature forms of human IP-10, e.g. after removal of the signal peptide (e.g. removal of residues 1-21 to leave residues 22-98 of SEQ ID NO:35 as the mature form). An amino acid sequence of a human (*Homo sapiens*) IP-10 used in the studies described herein and deposited in GenPept under accession number NP_001556 is presented as SEQ ID NO:35. The entire teachings of GenPept Accession Number NP_001556 are incorporated herein by reference. A receptor-binding fragment of human IP-10 can comprise fewer residues than the mature form, e.g., comprise at least about 5, 6, 7, 10, 15, 20 or more residues of SEQ ID NO:35. For example, receptor-binding fragments of human IP-10 include the N-terminus (about residues 22-29 of SEQ ID NO:35), the N-loop (about residues 33-38 of SEQ ID NO:35), the 40s-loop and the 30s-loop (see, e.g., Booth et al. (2002) *Biochemistry* 41:10418-10425).

"Human MIG" includes immature and mature forms of human MIG, e.g. after removal of the signal peptide (e.g. removal of residues 1-22 to leave residues 23-125 of SEQ ID NO:36 as the mature form). An amino acid sequence of a human (*Homo sapiens*) MIG used in the studies described herein and deposited in GenPept under accession number NP_002407 is presented as SEQ ID NO:36. The entire teachings of GenPept Accession Number NP_002407 are incorporated herein by reference. A receptor-binding variant of human MIG can include active secretion variants characterized by Liao et al. ((1995) *J. Exp. Med.* 182:1301-1314). A receptor-binding fragment of human MIG can comprise fewer residues than the mature form, e.g., comprise at least about 5, 6, 7, 10, 15, 20 or more residues of SEQ ID NO:36. For example, a receptor-binding fragment of human MIG can include the mature protein N-terminus and/or the N-loop of MIG (e.g. about amino acid residues 23-30 or 34-39 of SEQ ID NO:36, respectively). A receptor-binding fragment of human MIG can include at least the C-terminus of MIG (about amino acids 96-125 of SEQ ID NO:36, Clark-Lewis et al. (2003) *J. Biol. Chem.* 278:289-295).

"Human I-TAC" includes immature and mature forms of human I-TAC, e.g. after removal of the signal peptide (e.g. removal of residues 1-21 to leave residues 22-94 of SEQ ID NO:37 as the mature form). An amino acid sequence of a human (*Homo sapiens*) I-TAC used in the studies described herein and deposited in SwissProt under accession number O14625 is presented as SEQ ID NO:37. The entire teachings of SwissProt Accession Number O14625 are incorporated herein by reference. A receptor-binding fragment of human I-TAC can comprise fewer residues than the mature form, e.g., comprise at least about 5, 6, 7, 10, 15, 20 or more residues of SEQ ID NO:37. For example, receptor-binding fragments of human I-TAC include the mature protein N-terminus, the N-loop (e.g. about residues 33-38 of SEQ ID NO:37), and mature protein N-terminal deletion mutants (e.g. I-TAC mutants having residues 23-94 or 24-94 of SEQ ID NO:37) (see e.g., Clark-Lewis et al. (2003) *J. Biol. Chem.* 278:289-295).

Antibodies and Antibody Producing Cells

In the past, murine mAbs against human CXCR3 have been generated but most of them failed to completely inhibit binding of at least three ligands of CXCR3 tested, specifically IP-10, MIG and I-TAC. This may be explained by studies that suggest that ligands bind to CXCR3 differently from each other (Cox et al. (2001) *Mol. Pharmacol.* 59:707-715). In certain embodiments, antibodies (and cells which produce antibodies) that inhibit the binding of at least three ligands to human CXCR3 are provided. As described herein, human mAb 5H7 and human mAb 7H5 which each bind human CXCR3 were produced. Studies using these mAbs revealed that both human mAb 5H7 and human mAb 7H5 inhibited I-TAC induced chemotaxis of cells that expressed human CXCR3 in an in vitro assay. Further studies revealed that both human mAb 5H7 and human mAb 7H5 inhibited I-TAC-, IP-10- and MIG-induced chemotaxis of cells that expressed human CXCR3 in an in vitro assay.

The antibody of the invention can be polyclonal or monoclonal (mAb), and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein encompasses antigen-binding fragments of antibodies, including antigen-binding fragments of human, humanized, chimeric, CDR-grafted, veneered or single-chain antibodies and the like.

Antibodies which bind a CXCR3 protein can be selected from a suitable collection of natural or artificial antibodies or raised against an appropriate immunogen in a suitable host. For example, antibodies can be raised by immunizing a suitable host (e.g., mouse, human antibody-transgenic mouse, rat, rabbit, chicken, goat, non-human primate (e.g., monkey)) with a suitable immunogen, such as an isolated or purified CXCR3 protein, a cell expressing a recombinant CXCR3 protein (e.g., a cell that expresses an exogenous nucleic acid encoding human CXCR3 protein (CD183) (e.g. a CXCR3 transfectant)) or a chemically synthesized peptide of CXCR3, e.g. a peptide comprising at least 8, 9, 10, 11, 12, 15, 20, 25, 30, 33, 35, 37, or 40 residues of an extracellular sequence of human CXCR3 (e.g., a peptide having amino acid residues 1-37 or 191-223 of SEQ ID NO:2). In addition, cells expressing a recombinant CXCR3 protein, variant or ligand-binding fragment thereof, such as transfected cells, can be used in a screen for an antibody which binds thereto (See e.g., Chuntharapai et al., *J. Immunol.*, 152: 1783-1789 (1994); Chuntharapai et al., U.S. Pat. No. 5,440,021).

Preparation of the immunizing antigen, and polyclonal and monoclonal antibody production can be performed using any suitable technique. A variety of methods have been described. (See, e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991).) Generally, where a monoclonal antibody is desired, a hybridoma is produced by fusing a suitable cells from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans, human-antibody transgenic animals or other suitable animals immunized with the antigen of interest. Cells that produce antibodies of human origin (e.g., a human antibody) can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., *Hybridoma*, 17:299-304(1998); Zanella et al., *J Immunol Methods*, 156:205-215 (1992); Gustafsson et al., *Hum Antibodies Hybridomas*, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA).

Antibodies also can be prepared directly (e.g., synthesized or cloned) from an isolated antigen-specific antibody producing cell (e.g. a cell from the peripheral blood or, preferably the spleen or lymph nodes determined to produce an antibody with desired specificity), of humans, human-antibody transgenic animals or other suitable animals immunized with the antigen of interest (see, e.g. U.S. Pat. No. 5,627,052 (Schrader)).

Other suitable methods of producing or isolating antibodies or antigen-binding fragments of the desired specificity can be used, including, for example, methods which select a recombinant antibody or antigen-binding fragment thereof from a library, such as a phage display library. Such libraries can contain antibodies or antigen-binding fragments of antibodies that contain natural or artificial amino acid sequences. For example, the library can contain Fab fragments which contain artificial CDRs (e.g., random amino acid sequences) and human framework regions. (See, for example, U.S. Pat. No. 6,300,064 (Knappik, et al.), the entire teachings of which are incorporated herein by reference.)

Human antibodies and nucleic acids encoding same can be obtained from a human or from human-antibody transgenic animals. Human-antibody transgenic animals (e.g., mice) are animals that are capable of producing a repertoire of human antibodies, such as XENOMOUSE® (Abgenix, Fremont, Calif.), HUMAB-MOUSE®, KIRIN TC MOUSE® or KM-MOUSE® (MEDAREX®, Princeton, N.J.). Generally, the genome of human-antibody transgenic animals has been altered to include a transgene comprising DNA from a human immunoglobulin locus that can undergo functional rearrangement. An endogenous immunoglobulin locus in a human-antibody transgenic animal can be disrupted or deleted to eliminate the capacity of the animal to produce antibodies encoded by an endogenous gene. Suitable methods for producing human-antibody transgenic animals are well known in the art. (See, for example, U.S. Pat. Nos. 5,939,598 and 6,075, 181 (Kucherlapati et al.), U.S. Pat. Nos. 5,569,825, 5,545, 806, 5,625,126, 5,633,425, 5,661,016, and 5,789,650 (Lonberg et al.), Jakobovits et al., *Proc. Natl. Acad. Sci. USA*, 90: 2551-2555 (1993), Jakobovits et al. *Nature*, 362: 255-258 (1993), Jakobovits et al. WO 98/50433, Jakobovits et al. WO 98/24893, Lonberg et al. WO 98/24884, Lonberg et al. WO 97/13852, Lonberg et al. WO 94/25585, Lonberg et al. EP 0 814 259 A2, Lonberg et al. GB 2 272 440 A, Lonberg et al., *Nature* 368:856-859 (1994), Lonberg et al., *Int Rev Immunol* 13(1):65-93 (1995), Kucherlapati et al. WO 96/34096, Kucherlapati et al. EP 0 463 151 B1, Kucherlapati et al. EP 0 710 719 A1, Surani et al. U.S. Pat. No. 5,545,807, Bruggemann et al. WO 90/04036, Bruggemann et al. EP 0 438 474 B1, Taylor et al., *Int. Immunol.* 6(4)579-591 (1994), Taylor et al., *Nucleic Acids Research* 20(23):6287-6295 (1992), Green et al., *Nature Genetics* 7:13-21 (1994), Mendez et al., *Nature Genetics* 15:146-156 (1997), Tuaillon et al., *Proc Natl Acad Sci USA* 90(8):3720-3724 (1993) and Fishwild et al., *Nat Biotechnol* 14(7):845-851 (1996), the teachings of each of the foregoing are incorporated herein by reference in their entirety.)

As described herein, human-antibody transgenic animals can be immunized with a suitable composition comprising an antigen of interest (e.g., a recombinant cell expressing a CXCR3 protein). Antibody producing cells can be isolated and fused to form hybridomas using conventional methods.

Hybridomas that produce human antibodies having the desired characteristics (e.g., specificity, affinity) can be identified using any suitable assay (e.g., ELISA) and, if desired, selected and subcloned using suitable culture techniques.

Human-antibody transgenic animals provide a source of nucleic acids that can be enriched in nucleic acids that encode antibodies having desired properties, such as specificity and affinity. For example, nucleic acids encoding antibodies or antibody variable regions can be isolated from human-antibody transgenic mice that have been immunized with a CXCR3 protein. The isolated nucleic acids or portions thereof (e.g., portions encoding variable regions, CDRs, framework regions) can be expressed using any suitable method (e.g., phage display) to produce a library of antibodies or antigen-binding fragments of antibodies (e.g., single chain antigen-binding fragments, double chain antigen-binding fragments) that is enriched for antibodies or antigen-binding fragments that bind a CXCR3 protein. Such a library can exhibit enhanced diversity (e.g., combinatorial diversity through pairing of heavy chain variable regions and light chain variable regions) relative to the repertoire of antibodies produced in the immunized human-antibody transgenic animal. The library can be screened using any suitable assay (e.g., a CXCR3 protein binding assay) to identify antibodies or antigen-binding fragments having desired properties (e.g., specificity, affinity). The nucleic acids encoding antibody or antigen-binding fragments having desired properties can be recovered using any suitable method. (See, e.g., U.S. Pat. No. 5,871,907 (Winter et al.) and U.S. Pat. No. 6,057,098 (Buechler et al.), the entire teachings of each of the foregoing are incorporated herein by reference.)

An antibody of the invention can be a CDR-grafted (e.g., humanized) antibody or an antigen-binding fragment thereof. The CDRs of a CDR-grafted antibody can be derived from a suitable antibody which binds a CXCR3 protein (referred to as a donor antibody). For example, suitable CDRs can be derived from human mAb 5H7 or human mAb 7H5 which, as described herein, bind a CXCR3 protein (CD183) or from any other suitable antibody. Other sources of suitable CDRs include natural and artificial CXCR3 protein-specific antibodies obtained from nonhuman sources, such as rodent (e.g., mouse, rat, rabbit), chicken, pig, goat, non-human primate (e.g., monkey) or non-human library.

The framework regions of a CDR-grafted antibody are preferably of human origin, and can be derived from any human antibody variable region having sequence similarity to the analogous or equivalent region (e.g., heavy chain variable region or light chain variable region) of the antigen-binding region of the donor antibody. Other sources of framework regions of human origin include human variable region consensus sequences. (See, e.g., Kettleborough, C. A. et al., *Protein Engineering* 4:773-783 (1991); Carter et al., WO 94/04679; Kabat, E. A., et al., *Sequences of Proteins of Immunological Interest*, Fifth Edition, U.S. Department of Health and Human Services, U.S. Government Printing Office (1991)).

In one embodiment, the framework regions of a CDR-grafted (e.g., humanized) antibody chain can be derived from a variable region of human origin having at least about 65% overall amino acid sequence identity, and preferably at least about 70% overall amino acid sequence identity, with the amino acid sequence of the variable region of the donor antibody. A suitable framework region can also be derived from an antibody of human origin having at least about 65% amino acid sequence identity, and preferably at least about 70%, 80%, 90% or 95% amino acid sequence identity over the length of the framework region within the amino acid sequence of the equivalent portion (e.g., framework region) of the donor antibody. For example, a suitable framework region of human origin can be derived from an antibody of human origin (e.g., a human antibody) having at least about 65% amino acid sequence identity, and preferably at least about 70%, 80%, 90% or 95% amino acid sequence identity, over the length of the particular framework region being used, when compared to the amino acid sequence of the equivalent portion (e.g., framework region) of the donor antibody. Amino acid sequence identity can be determined using a suitable amino acid sequence alignment algorithm, such as CLUSTAL W, using the default parameters. (Thompson J. D. et al., *Nucleic Acids Res*. 22:4673-4680 (1994).)

Framework regions of human origin can include amino acid substitutions or replacements, such as "back mutations" which replace an amino acid residue in the framework region of human origin with a residue from the corresponding position of the donor antibody. One or more mutations in the framework region can be made, including deletions, insertions and substitutions of one or more amino acids. Preferably, the CDR-grafted (e.g., humanized) antibody binds a CXCR3 protein with an affinity similar to, substantially the same as, or better than that of the donor antibody. Variants can be produced by a variety of suitable methods, including mutagenesis of nonhuman donor or acceptor human chains. (See, e.g., U.S. Pat. No. 5,693,762 (Queen et al.) and U.S. Pat. No. 5,859,205 (Adair et al.), the entire teachings of which are incorporated herein by reference.)

Constant regions of antibodies, antibody chains (e.g., heavy chain, light chain) or fragments or portions thereof of the invention, if present, can be derived from any suitable source. For example, constant regions of human, humanized and certain chimeric antibodies, antibody chains (e.g., heavy chain, light chain) or fragments or portions thereof, if present can be of human origin and can be derived from any suitable human antibody or antibody chain. For example, a constant region of human origin or portion thereof can be derived from a human κ or λ light chain, and/or a human γ (e.g., γ1, γ2, γ3, γ4), μ, α (e.g., α1, α2), δ or ε heavy chain, including allelic variants. In certain embodiments, the antibody or antigen-binding fragment (e.g., antibody of human origin, human antibody) can include amino acid substitutions or replacements that alter or tailor function (e.g., effector function). For example, a constant region of human origin (e.g., γ1 constant region, γ2 constant region) can be designed to reduce complement activation and/or Fc receptor binding. (See, for example, U.S. Pat. No. 5,648,260 (Winter et al.), U.S. Pat. No. 5,624,821 (Winter et al.) and U.S. Pat. No. 5,834,597 (Tso et al.), the entire teachings of which are incorporated herein by reference.) Preferably, the amino acid sequence of a constant region of human origin that contains such amino acid substitutions or replacements is at least about 95% identical over the full length to the amino acid sequence of the unaltered constant region of human origin, more preferably at least about 99% identical over the full length to the amino acid sequence of the unaltered constant region of human origin.

Humanized antibodies or antigen-binding fragments of a humanized antibody can be prepared using any suitable method. Several such methods are well-known in the art. (See, e.g., U.S. Pat. No. 5,225,539 (Winter), U.S. Pat. No. 5,530,101 (Queen et al.).) The portions of a humanized antibody (e.g., CDRs, framework, constant region) can be obtained or derived directly from suitable antibodies (e.g., by de novo synthesis of a portion), or nucleic acids encoding an antibody or chain thereof having the desired property (e.g., binds a CXCR3 protein) can be produced and expressed. Humanized immunoglobulins comprising the desired portions (e.g., CDR, FR, constant region) of human and nonhuman origin can be produced using synthetic and/or recombinant nucleic acids to prepare a nucleic acid (e.g., cDNA) encoding the desired humanized chain. To prepare a portion of a chain, one or more stop codons can be introduced at the desired position. For example, nucleic acid (e.g., DNA) sequences coding for newly designed humanized variable regions can be constructed using PCR mutagenesis methods to alter existing DNA sequences. (See, e.g., Kamman, M., et al., *Nucl. Acids Res*. 17:5404 (1989).) PCR primers coding for the new CDRs can be hybridized to a DNA template of a previously humanized variable region which is based on the same, or a very similar, human variable region (Sato, K., et al., *Cancer Research* 53:851-856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971-980 (1993)). A sequence encoding a signal peptide can also be incorporated into the nucleic acid (e.g., on synthesis, upon insertion into a vector). The natural signal peptide sequence from the acceptor antibody, a signal peptide sequence from another antibody or other suitable sequence can be used (see, e.g., Kettleborough, C.A., *Protein Engineering* 4:773-783 (1991)). Using these methods, methods described herein or other suitable methods, variants can be readily produced. In one embodiment, cloned variable regions can be mutated, and sequences encoding variants with the desired specificity can be selected (e.g., from a phage library; see, e.g., U.S. Pat. No. 5,514,548 (Krebber et al.) and WO 93/06213 (Hoogenboom et al.)).

The antibody of the invention can be a chimeric antibody or an antigen-binding fragment of a chimeric antibody. Preferably, the chimeric antibody or antigen-binding fragment thereof comprises a variable region of non-human origin and a constant region of human origin (e.g., a human constant region).

Chimeric antibodies and antigen-binding fragments of chimeric antibodies that bind a CXCR3 protein can be prepared using any suitable method. Several suitable methods are well-known in the art. (See, e.g., U.S. Pat. No. 4,816,567 (Cabilly et al.), U.S. Pat. No. 5,116,946 (Capon et al.).) Generally, chimeric antibodies are produced by preparing, for each of the light and heavy chain components of the chimeric immunoglobulin, a recombinant nucleic acid comprising a first nucleotide sequence encoding at least the variable region of an antibody from a first species that binds a CXCR3 protein that is joined in-frame to a second nucleotide sequence encoding at least a part of a constant region from an antibody of a different species. Generally, the recombinant nucleic acid encodes a chimeric heavy chain or a chimeric light chain. However, if desired, a single recombinant nucleic acid encoding a chimeric heavy chain and a chimeric light chain can be prepared. The recombinant nucleic acids can be assembled in or inserted into an expression vector. The recombinant nucleic acid(s) can be introduced into a suitable host cell that is capable of expressing the chimeric antibody or chimeric antibody chain using any suitable method (e.g., transfection, transformation, infection) to produce a recombinant host cell. The recombinant host cell can be maintained under conditions suitable for expression of the chimeric antibody or chimeric antibody chain and the antibody or chain can be recovered.

Nucleic acids encoding the variable region of antibody light and heavy chains can be obtained from cells (e.g., B cells, hybridoma cells) that produce an antibody that binds a CXCR3 protein. For example, nucleic acids that encode human heavy and light chain variable regions that can bind a CXCR3 protein can be obtained from hybridoma 5H7 and hybridoma 7H5 described herein. Nucleic acids that encode constant regions can be obtained from suitable sources using any suitable technique, such as conventional techniques of recombinant DNA technology. The nucleotide sequences of nucleic acids encoding human κ or λ light chain constant regions, and γ (e.g., γ1, γ2, γ3, γ4), μ, α (e.g., α1, α2), δ or ε human heavy chain constant regions are readily available.

The invention also relates to a bispecific antibody or antigen-binding fragment thereof (e.g., F(ab')$_2$), which binds a CXCR3 protein and at least one other antigen. In a particular embodiment, the bispecific antibody, or antigen-binding fragment thereof binds an epitope on a CXCR3 protein. In other embodiments, the bispecific antibody or antigen-binding fragment thereof has the epitopic specificity of human mAb 5H7 or human mAb 7H5 and at least one other antibody. Bispecific antibodies can be secreted by triomas and hybrid hybridomas. Generally, triomas are formed by fusion of a hybridoma and a lymphocyte (e.g., antibody secreting B cell) and hybrid hybridomas are formed by fusion of two hybridomas. Each of the cells that are fused to produce a trioma or hybrid hybridoma produces a monospecific antibody. However, triomas and hybrid hybridomas can produce an antibody containing antigen-binding sites which recognize different antigens. The supernatants of triomas and hybrid hybridomas can be assayed for bispecific antibody using a suitable assay (e.g., ELISA), and bispecific antibodies can be purified using conventional methods. (See, e.g., U.S. Pat. No. 5,959,084 (Ring et al.) U.S. Pat. No. 5,141,736 (Iwasa et al.), U.S. Pat. Nos. 4,444,878, 5,292,668 and 5,523,210 (Paulus et al.) and U.S. Pat. No. 5,496,549 (Yamazaki et al.).)

The various portions of an antibody (e.g., mouse antibody, human antibody, humanized antibody, chimeric antibody and antigen-binding fragments of the foregoing) can be joined together chemically using conventional techniques, or can be prepared as a continuous polypeptide chain by expression (in vivo or in vitro) of a nucleic acid (one or more nucleic acids) encoding antibody. For example, nucleic acids encoding a human, humanized or chimeric chain can be expressed in vivo or in vitro to produce a continuous polypeptide chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

The invention also relates to antigen-binding fragments of antibodies, antibody chains and antigen-binding portions of antibody chains that retain the capacity to bind antigen (e.g., a CXCR3 protein). Such antigen-binding fragments of antibodies retain the antigen-binding function of a corresponding full-length antibody (e.g., binding specificity for a CXCR3 protein), and preferably inhibit binding of ligand (e.g., IP-10, MIG or I-TAC) to a CXCR3 protein. Antigen-binding fragments of antibodies encompassed by the invention include, Fv fragments (e.g., single chain Fv fragments (scFv)), Fab fragments, Fab' fragments and F(ab')$_2$ fragments, for example. Such antigen-binding fragments can be produced using any suitable method, for example by enzymatic cleavage and/or using recombinant DNA technology. For example, an antibody can be cleaved with papain or pepsin to yield a Fab fragment or F(ab')$_2$ fragment, respectively. Other proteases with the requisite substrate specificity can also be used to generate antigen-binding fragments of antibodies, such as Fab fragments or F(ab')$_2$ fragments and variable domains ($V_H$, $V_L$). Similarly, Fv fragments can be prepared by digesting an antibody with a suitable protease or using recombinant DNA technology. For example, a nucleic acid can be prepared that encodes a light chain variable region and heavy chain variable region that are connected by a suitable peptide linker, such as a chain of two to about twenty glycyl residues. The nucleic acid can be introduced into a suitable host (e.g., E. coli) using any suitable technique (e.g., transfection, transformation, infection), and the host can be maintained under conditions suitable for expression of a single chain Fv fragment. A variety of antigen-binding fragments of antibodies can be prepared using antibody genes in which one or more stop codons has been introduced upstream of the natural stop site. For example, an expression construct encoding a F(ab')$_2$ portion of an immunoglobulin heavy chain can be designed by introducing a translation stop codon at the 3' end of the sequence encoding the hinge region of the heavy chain.

The invention also relates to the individual heavy and light chains of the antibodies (e.g., mouse antibodies, human antibodies, humanized antibodies, chimeric antibodies) that bind a CXCR3 protein and to antigen-binding portions thereof. The heavy chains or light chains (and antigen-binding portions thereof) of the invention can bind a CXCR3 protein individually, and/or when paired with a complementary light or heavy chain, respectively. Complementary chains can be identified using any suitable method (e.g., phage display, transgenic animals). For example, a transgenic animal comprising a functionally rearranged nucleic acid encoding a desired heavy chain can be prepared. The heavy-chain transgenic animal can be immunized with the antigen of interest and hybridomas produced. Because of allelic exclusion at immunoglubulin loci, the heavy-chain transgenic mouse may not significantly express endogenous heavy chains and substantially all antibodies elicited by immunization can comprise the heavy chain of interest and a complementary light chain.

The antigen-binding properties (e.g., specificity, affinity) of antibodies and antigen-binding fragments of antibodies can be elucidated using any suitable method. For example, binding specificity can be determined using assays in which formation of a complex between antibody or antigen-binding fragment thereof and a CXCR3 protein, is detected or measured. Compositions which comprise a CXCR3 protein and which can be used to assess antigen-binding properties of the antibodies and antigen-binding fragments described herein include a membrane fraction of a cell comprising a CXCR3 protein, a cell bearing a CXCR3 protein, such as a human lymphocyte, human lymphocyte cell line, a recombinant host cell comprising a nucleic acid encoding a CXCR3 protein which expresses a CXCR3 protein, a synthetic peptide and the like. Binding and/or functional assays or other suitable methods also can be used in procedures for the identification and/or isolation of antibodies (e.g., human and/or humanized antibodies) having the requisite specificity (e.g., an assay in which binding between a cell bearing a CXCR3 protein and a ligand thereof (e.g., IP-10, MIG or I-TAC, an immobilized IP-10, MIG or I-TAC fusion protein (e.g., IP-10-, MIG- or I-TAC-Fc fusion protein) is detected and/or measured (e.g. in a binding assay or in an assay measuring CXCR3-mediated function, e.g. intracellular calcium release or chemotaxis), or another suitable method.

The antibodies of the invention bind a human CXCR3 protein. In some embodiments, the antibody binds a CXCR3 protein and inhibits binding of a ligand, such as IP-10, MIG or I-TAC, to the CXCR3 protein. For example, the antibody can inhibit a CXCR3-mediated function of a cell expressing a CXCR3 protein (e.g., signal transduction, intracellular calcium release, chemotaxis, cell differentiation, cell proliferation or cell activation). In a preferred embodiment, the antibody of the invention binds a CXCR3 protein and inhibits binding of at least two, preferably at least three ligands, IP-10, MIG and I-TAC, to the CXCR3 protein.

Preferred antibodies which bind a CXCR3 protein include chimeric antibodies, humanized antibodies and antigen-binding fragments of the foregoing. Particularly preferred antibodies are human antibodies and antigen-binding fragments of human antibodies. As described herein, human antibodies designated human mAb 5H7 and human mAb 7H5 which bind a CXCR3 protein have been produced. Both human mAb 5H7 and human mAb 7H5 were produced as IgG2, kappa antibodies in the original hybridomas, as described herein. The nucleic acid sequences encoding the heavy and light chain variable regions of human mAb 5H7 were cloned into a vector, pLKTOK59(D). The resulting construct encoded an IgG1, kappa antibody with the variable regions and binding specificity of human mAb 5H7.

Human mAb 5H7 (IgG2, kappa) can be produced by hybridoma 5H7, also referred to as hybridoma LS328-5H7-2-6, which was deposited on Aug. 7, 2003, on behalf of Millennium Pharmaceuticals Inc., 75 Sidney Street, Cambridge, Mass., 02139, USA, at the American Type Culture Collection, 10801 University Boulevard, Manassas, Va. 20110, U.S.A., under Accession No. PTA-5388. The invention relates to hybridoma 5H7, to the antibody it produces, antigen-binding fragments thereof, and to nucleic acids encoding the antibody and portions thereof (e.g., heavy chain, heavy chain variable region, light chain, light chain variable region). As described herein, hybridoma 5H7 produces an IgG2, kappa antibody.

Human mAb 7H5 can be produced by hybridoma 7H5, also referred to as hybridoma LS329-7H5-2-19-7, which was deposited on Aug. 7, 2003, on behalf of Millennium Pharmaceuticals Inc., 75 Sidney Street, Cambridge, Mass., 02139, USA, at the American Type Culture Collection, 10801 University Boulevard, Manassas, Va. 20110, U.S.A., under Accession No. PTA-5389. The invention relates to hybridoma 7H5, to the antibody it produces, antigen-binding fragments thereof, and to nucleic acids encoding the antibody and portions thereof (e.g., heavy chain, heavy chain variable region, light chain, light chain variable region). As described herein, hybridoma 7H5 produces an IgG2, kappa antibody.

In one embodiment, the antibody or antigen-binding fragment thereof can bind to the same or similar epitope as human mAb 5H7 or human mAb 7H5. Antibodies and antigen-binding fragments that bind the same or similar epitope as human mAb 5H7 or human mAb 7H5 can be identified using any suitable method, such as a competitive binding assay. For example, an antibody can be tested for the ability to competitively inhibit binding of human mAb 5H7 or human mAb 7H5 to a CXCR3 protein expressed on the surface of a cell. Competitive inhibition of binding of human mAb 5H7 or human mAb 7H5 in this type of assay is indicative that the test antibody binds the same or similar epitope as human mAb 5H7 or human mAb 7H5.

In particular embodiments, the antibody or antigen-binding fragment thereof can have the epitopic specificity of human mAb 5H7 or human mAb 7H5. The fine epitopic specificity of an antibody can be determined using any suitable method, such as peptide competition or mutational analysis. For example, a series of CXCR3 variants comprising amino acid replacements can be prepared and an antibody can be tested for the ability to bind each variant. Inhibited or abrogated binding to a variant comprising a particular amino acid substitution is indicative that the substituted amino acid is part of the epitope that the antibody binds. (See, Higgins et al., *J. Biol. Chem.* 275:25652-25664 (2000).)

Isolated antibodies or antigen-binding fragments of the invention typically bind to a CXCR3 protein with a binding equilibrium association constant (KA) of at least about $10^6$ $M^{-1}$, at least about $10^7 M^{-1}$, preferably at least about $10^8 M^{-1}$, more preferably, at least about $10^9 M^{-1}$, and more preferably at least about $10^{10}$ to about $10^{11} M^{-1}$ or higher.

As used herein, an "antigen-binding portion" of an antibody comprises a portion of a variable region of an antibody, said portion comprising at least one, two, preferably three CDRs selected from CDR1, CDR2, and CDR3. The antigen-binding portion can comprise a portion of an immunoglobulin heavy chain or an immunoglobulin light chain.

In more particular embodiments, the antibody comprises one, two or three heavy chain complementarity determining regions (HCDR1, HCDR2 and/or HCDR3) having the amino acid sequences of heavy chain CDR1, CDR2 and CDR3 of human mAb 5H7. If desired, one amino acid residue in the heavy chain CDR1, one or two amino acid residues in the heavy chain CDR2, and/or one, two or three amino acid residues in CDR3 can be conservatively substituted. The antibody can further comprise one, two or three light chain complementarity determining regions (LCDR1, LCDR2 and/or LCDR3) having the amino acid sequences of light chain CDR1, CDR2 and CDR3 of human mAb 5H7. If desired, one or two amino acid residues in the light chain CDR1, one amino acid residue in the light chain CDR2 and/or one or two amino acid residues in the light chain CDR3 can be conservatively substituted. Preferably, the antibody comprises the three heavy chain CDRs and the three light chain CDRs of human mAb 5H7. In more particular embodiments, the antibody comprises the heavy chain variable region of human mAb 5H7 (5H7 VH, SEQ ID NO: 2) and the light chain variable region of human mAb 5H7 (5H7 VK, SEQ ID NO:10).

In additional particular embodiments, the antibody comprises one, two or three heavy chain complementarity determining regions (HCDR1, HCDR2 and/or HCDR3) having the amino acid sequences of the heavy chain CDR1, CDR2, and CDR3 of human mAb 7H5. If desired, one amino acid residue in the heavy chain CDR1, one or two amino acid residues in the heavy chain CDR2 and/or one, two or three amino acid residues in the heavy chain CDR3 can be conservatively substituted. The antibody can further comprise one, two or three light chain complementarity determining regions (LCDR1, LCDR2 and/or LCDR3) having the amino acid sequences of the light chain CDR1, CDR2, and CDR3 of human mAb 7H5. If desired, one or two amino acid residues in the light chain CDR1, one amino acid residue in the light chain CDR2 and/or one or two amino acid residues in the light chain CDR3 can be conservatively substituted. Preferably, the antibody comprises the three heavy chain CDRs and the three light chain CDRs of human mAb 7H5. In more particular embodiments, the antibody comprises the heavy chain variable region of human mAb 7H5 (7H5 VH, SEQ ID NO:18) and the light chain variable region of human mAb 7H5 (7H5 VK, SEQ ID NO:26).

The sequence ID numbers of the immuglobulin heavy and light chain variable regions and respective CDRs of human mAb 5H7 and human mAb 7H5 are listed below in Tables 1 and 2.

TABLE 1

Sequence ID Numbers of Variable Regions of Human Monoclonal 5H7 Antibody

| Chain | Portion | Type | Length | SEQ ID NO: |
|---|---|---|---|---|
| Heavy (5H7 VH) | Full Length | DNA | 378 | 1 |
| | Full Length | aa | 126 | 2 |
| | CDR1 | DNA | 15 | 3 |
| | CDR1 | aa | 5 | 4 |
| | CDR2 | DNA | 51 | 5 |
| | CDR2 | aa | 17 | 6 |
| | CDR3 | DNA | 51 | 7 |
| | CDR3 | aa | 17 | 8 |
| Light (5H7 VK) | Full Length | DNA | 321 | 9 |
| | Full Length | aa | 107 | 10 |
| | CDR1 | DNA | 33 | 11 |
| | CDR1 | aa | 11 | 12 |
| | CDR2 | DNA | 21 | 13 |
| | CDR2 | aa | 7 | 14 |
| | CDR3 | DNA | 27 | 15 |
| | CDR3 | aa | 9 | 16 |

TABLE 2

Sequence ID Numbers of Variable Regions of Human Monoclonal 7H5 Antibody

| Chain | Portion | Type | Length | SEQ ID NO: |
|---|---|---|---|---|
| Heavy (7H5 VH) | Full Length | DNA | 378 | 17 |
| | Full Length | aa | 126 | 18 |
| | CDR1 | DNA | 15 | 19 |
| | CDR1 | aa | 5 | 20 |
| | CDR2 | DNA | 51 | 21 |
| | CDR2 | aa | 17 | 22 |
| | CDR3 | DNA | 51 | 23 |
| | CDR3 | aa | 17 | 24 |
| Light (7H5 VK) | Full Length | DNA | 321 | 25 |
| | Full Length | aa | 107 | 26 |
| | CDR1 | DNA | 33 | 27 |
| | CDR1 | aa | 11 | 28 |
| | CDR2 | DNA | 21 | 29 |
| | CDR2 | aa | 7 | 30 |
| | CDR3 | DNA | 27 | 31 |
| | CDR3 | aa | 9 | 32 |

In additional embodiments, the invention provides novel heavy chains and light chains of the antibodies and antigen-binding fragments described herein. In particular embodiments, the antibody heavy chains or antigen-binding portions thereof comprise at least one, two, preferably three CDRs having amino acid sequences of the heavy chain CDRs of human mAb 5H7 or the heavy chain CDRs of human mAb 7H5. For example, the antibody heavy chains or antigen-binding portions thereof can comprise an amino acid sequence selected from the group consisting of SEQ ID NO:4, SEQ ID NO:6, SEQ ID NO:8, SEQ ID NO:20, SEQ ID NO:22, and SEQ ID NO:24. If desired, residues in each heavy chain CDR can be conservatively substituted as described above. In preferred embodiments, the antibody heavy chains or antigen-binding portions thereof comprise three CDRs which have the amino acid sequences of the three CDRs of the heavy chain of human mAb 5H7 or the three CDRs of the heavy chain of human mAb 7H5. In other embodiments, the antibody heavy chains or antigen-binding portions thereof comprise the heavy chain variable region of human mAb 5H7 or human mAb 7H5. For example, the antibody heavy chains can comprise an amino acid sequence selected from the group consisting of SEQ ID NO: 2 and SEQ ID NO: 18. The antibody heavy chains and portions thereof can comprise any suitable framework regions and/or constant region.

In certain embodiments, the antibody light chains or antigen-binding portions thereof comprise at least one, two, preferably three CDRs having amino acid sequences of the light chain CDRs of human mAb 5H7 or the light chain CDRs of human mAb 7H5. For example, the antibody light chains or antigen-binding portions thereof can comprise an amino acid sequence selected from the group consisting of SEQ ID NO:12, SEQ ID NO:14, SEQ ID NO:16, SEQ ID NO:28, SEQ ID NO:30, and SEQ ID NO:32. If desired, residues in each light chain CDR can be conservatively substituted as described above. In preferred embodiments, the antibody light chains or antigen-binding portions thereof comprise three CDRs which have the amino acid sequences of the three CDRs of the light chain of human mAb 5H7 or the three CDRs of the light chain of human mAb 7H5. In other embodiments, the antibody light chains or antigen-binding portions thereof comprise the light chain variable region of human mAb 5H7 or human mAb 7H5. For example, the antibody light chains can comprise an amino acid sequence selected from the group consisting of SEQ ID NO: 10 and SEQ ID NO: 26. The antibody light chains and portions thereof can comprise any suitable framework regions and/or constant region.

Fusion Proteins and Immuno-Conjugates

Fusion proteins and immuno-conjugates can be produced in which an antibody moiety (e.g., antibody or antigen-binding fragment thereof, antibody chain or antigen-binding portion thereof) is linked directly or indirectly to a non-immunoglobulin moiety (i.e., a moiety which does not occur in immunoglobulins as found in nature). Fusion proteins comprise an antibody moiety and a non-immunoglobulin moiety that are components of a single continuous polypeptide chain. The non-immunoglobulin moiety can be located N-terminally, C-terminally or internally with respect to the antibody moiety. For example, some embodiments can be produced by the insertion of a nucleic acid encoding immunoglobulin sequences into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be expressed (e.g., in vivo by a suitable host cell, in vitro) to produce antibody chains that comprise a non-immunoglobulin moiety (e.g., Histidine tag, E tag, Protein A IgG binding domain). Fusion proteins can be isolated or recovered using any suitable technique, such as chromatography using a suitable affinity matrix (see e.g., *Current Protocols in Molecular Biology* (Ausubel, F. M. et al., eds., Vol. 2, Suppl. 26, pp. 16.4.1-16.7.8 (1991)).

In other embodiments, the antibody moiety and non-immunoglobulin moiety may not be part of a continuous polypeptide chain, but can be connected or conjugated directly or indirectly through any suitable linker. Suitable methods for connecting or conjugating the moieties are well known in the art. (See, e.g., Ghetie et al., *Pharmacol. Ther.* 63:209-34 (1994)). A variety of suitable linkers (e.g., heterobifunctional reagents) and methods for preparing immuno-conjugates are well known in the art. (See, for example, Hermanson, G. T., *Bioconjugate Techniques*, Academic Press: San Diego, Calif. (1996).) The non-immunoglobulin moiety can be bonded to a chemically reactive group on the antibody moiety, e.g., to a free amino, imino, hydroxyl, thiol or carboxyl group (e.g., the N- or C-terminus, to the epsilon amino group of one or more lysine residue or to the sulfhydryl of one or more cysteinyl residue). The site to which the non-immunoglobulin moiety is bound can be a natural residue in the amino acid sequence of the antibody moiety or it can be introduced in the antibody moiety, e.g., by DNA recombinant technology (e.g., by introducing a cysteine or a protease cleavage site in the amino acid sequence) or by protein biochemistry, e.g., reduction, pH adjustment or proteolysis. The immuno-conjugate can be purified from reactants by employing methodologies, e.g., column chromatography (e.g., affinity chromatography, ion exchange chromatography, gel filtration, hydrophobic interaction chromatography), dialysis, diafiltration or precipitation, well known to those of skill in the art. The immuno-conjugate can be evaluated by employing methodologies, e.g., SDS-PAGE, mass spectroscopy or capillary electrophoresis, well known to those skilled in the art.

Suitable non-immunoglobulin moieties for inclusion in an immuno-conjugate include a therapeutic moiety, such as a toxin (e.g., cytotoxin, cytotoxic agent), a therapeutic agent (e.g., a chemotherapeutic agent), an antimetabolite, an alkylating agent, an anthracycline, an antibiotic, an anti-mitotic agent, a biological response modifier (e.g., a cytokine (e.g., an interleukin, an interferon, a tumor necrosis factor), a growth factor (e.g., a neurotrophic factor)), a plasminogen activator, a radionuclide (e.g., a radioactive ion), an enzyme) or a detectable label, e.g., a radionuclide (e.g., technetium-99m, indium-111), and the like. Another suitable non-immunoglobulin moiety for inclusion in an immuno-conjugate includes an organic moiety intended to increase the in vivo serum half-life of the antibody.

Suitable cytotoxins or cytotoxic agents include any agent that is detrimental to cells. Examples of suitable cytotoxins or cytotoxic agents include cytochalasin B, gramicidin D, ethidium bromide, emetine, mitomycin (e.g., mitomycin C), etoposide, tenoposide, doxorubicin, daunorubicin, dihydroxy anthracindione, mitoxantrone, mithramycin, actinomycin D, 1-dehydrotestosterone, glucocorticoids, procaine, tetracaine, lidocaine, propranolol, puromycin, and analogs or homologs of any of the foregoing agents.

Suitable therapeutic agents include, but are not limited to, antimetabolites (e.g., methotrexate, 6-mercaptopurine, 6-thioguanine, cytarabine, 5-fluorouracil decarbazine), alkylating agents (e.g., meclilorethamine, thioepachlorambucil, CC-1065, melphalan, carrnustine (BSNU), lomustine (CCNU), cyclophosphamide, busulfan, dibromomannitol, streptozotocin, mitomycin C, and cis-dichiorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithrainycin, and anthramycin (AMC)), and anti-mitotic agents (e.g., vincristine, vinbiastine, coichicines, TAXOL® (paclitaxel, Bristol-Myers Squibb Company) and maytansinoids (e.g., maytansinol (see U.S. Pat. No. 5,208,020), CC-1065 (see U.S. Pat. Nos. 5,475,092, 5,585,499, 5,846,545), DM1)). Suitable radionuclide therapeutic agents include, for example iodine (e.g., iodine-125, -126), yttrium (e.g., yttrium-90, -91) and praseodymium (e.g., praseodymium-144, -145).

In certain embodiments, the therapeutic agent can be a protein or polypeptide possessing a desired biological activity. Such proteins or polypeptides can include, for example, a toxin such as abrin, ricin A, pseudomonas exotoxin, or diphtheria toxin; a protein such as a tumor necrosis factor (e.g., TNFα, TNFβ), and interferon (e.g., α-interferon, β-interferon, γ-interferon), a neurotrophic factor (e.g., nerve growth factor), a growth factor (e.g., platelet derived growth factor), a plasminogen activator (e.g., tissue plasminogen activator); or biological response modifiers such as, for example, cytokines and lymphokines, (e.g., interleukin-1 ("IL-1"), interleukin-2 ("IL-2"), interleukin-6 ("IL-6"granulocyte macrophase colony stimulating factor ("GM-CSF"), granulocyte colony stimulating factor ("G-CSF")), or other growth factors. In other embodiments, the antibody or antigen-binding fragment of the invention can be conjugated to a second antibody or antigen-binding fragment to form an antibody heteroconjugate. (See, e.g., U.S. Pat. No. 4,676,980 (Segal).)

Suitable organic moieties intended to increase the in vivo serum half-life of the antibody can include one, two or more linear or branched moiety selected from a hydrophilic polymeric group (e.g., a linear or a branched polymer (e.g., a polyalkane glycol such as polyethylene glycol, monomethoxy-polyethylene glycol and the like), a carbohydrate (e.g., a dextran, a cellulose, a polysaccharide and the like), a polymer of a hydrophilic amino acid (e.g., polylysine, polyaspartate and the like), a polyalkane oxide and polyvinyl pyrolidone), a fatty acid group (e.g., a mono-carboxylic acid or a di-carboxylic acid), a fatty acid ester group, a lipid group (e.g., diacylglycerol group, sphingolipid group (e.g., ceramidyl)) or a phosopholipid group (e.g., phosphatidyl ethanolamine group). Preferably, the organic moiety is bound to a predetermined site where the organic moiety does not impair the function (e.g., decrease the antigen binding affinity) of the resulting immuno-conjugate compared to the non-conjugated antibody moiety. The organic moiety can have a molecular weight of about 500 Da to about 50,000 Da, preferably about 2000, 5000, 10,000 or 20,000 Da. Examples and methods for modifying polypeptides, e.g., antibodies, with organic moieties can be found, for example, in U.S. Pat. Nos. 4,179,337 and 5,612,460, PCT Publication Nos. WO 95/06058 and WO 00/26256, and U.S. Pat. Application Publication No. 20030026805, the entire teachings of which are incorporated herein by reference.

Nucleic Acids and Constructs

The present invention also relates to isolated and/or recombinant (including, e.g., essentially pure) nucleic acids comprising sequences which encode an antibody or antigen-binding fragment (e.g., a human, humanized, chimeric antibody or light or heavy chain of any of the foregoing) or fusion protein of the invention.

Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a vector (e.g., a plasmid). Nucleic acids can be naturally occurring, produced by chemical synthesis, by combinations of biological and chemical methods (e.g., semisynthetic), and be isolated using any suitable methods.

Nucleic acids referred to herein as "recombinant" are nucleic acids which have been produced by recombinant DNA methodology, including methods which rely upon artificial recombination, such as cloning into a vector or chromosome using, for example, restriction enzymes, homologous recombination, viruses and the like, and nucleic acids prepared using the polymerase chain reaction (PCR). "Recombinant" nucleic acids are also those that result from recombination of endogenous or exogenous nucleic acids through the natural mechanisms of cells or cells modified to allow recombination (e.g., cells modified to express Cre or other suitable recombinase), but are selected for after the introduction to the cells of nucleic acids designed to allow and make recombination probable. For example, a functionally rearranged human-antibody transgene is a recombinant nucleic acid.

The present invention also relates more specifically to nucleic acids that encode the heavy chains and/or light chains of the antibodies and antigen-binding portions described herein. For example, in one embodiment, the nucleic acid can encode a heavy chain or antigen-binding portion thereof that comprises at least one, two or preferably three CDRs having the amino acid sequences of the heavy chain CDRs of human mAb 5H7 wherein, optionally, one, two or three amino acids in each CDR can be conservatively substituted as described above. In another embodiment, the nucleic acid can encode a heavy chain or antigen-binding portion thereof that comprises at least one, two or preferably three CDRs having the amino acid sequences of the heavy chain CDRs of human mAb 7H5 wherein, optionally, one, two or three amino acids in each CDR can be conservatively substituted as described above. In preferred embodiments, the nucleic acid encodes an antibody heavy chain or antigen-binding portion thereof that comprises three CDRs that have the amino acid sequences of the three CDRs of the heavy chain of human mAb 5H7 or the three CDRs of the heavy chain of human mAb 7H5. In other embodiments, the nucleic acid encodes an antibody heavy chain or antigen-binding portion thereof that comprises the heavy chain variable region of human mAb 5H7 or human mAb 7H5. For example, the nucleic acid can comprise a nucleotide sequence selected from the group consisting of SEQ ID NO: 1 and SEQ ID NO: 17. The antibody heavy chains and portions thereof can further comprise any suitable framework regions and/or constant region.

In another embodiment, the nucleic acid can encode a light chain or antigen-binding portion thereof that comprises at least one, two, preferably three CDRs having the amino acid sequences of the light chain CDRs of human mAb 5H7 wherein, optionally, one or two amino acids in each CDR can be conservatively substituted as described above. In another embodiment, the nucleic acid can encode a light chain or antigen-binding portion thereof that comprises at least one, two, preferably three CDRs having the amino acid sequences of the light chain CDRs of human mAb 7H5 wherein, optionally, one or two amino acids in each CDR can be conservatively substituted as described above. In preferred embodiments, the nucleic acid encodes an antibody light chain or antigen-binding portion thereof which comprises three CDRs which have the amino acid sequences of the three CDRs of the light chain of human mAb 5H7 or the three CDRs of the light chain of human mAb 7H5. In other embodiments, the nucleic acid encodes an antibody light chain or antigen-binding portion thereof which comprises the light chain variable region of human mAb 5H7 or human mAb 7H5. For example, the nucleic acid can comprise a nucleotide sequence selected from the group consisting of SEQ ID NO: 9 and SEQ ID NO: 25. The antibody light chains and portions thereof can comprise any suitable framework regions and/or constant region.

Nucleic acid molecules of the present invention can be used in the production of antibodies (e.g., human antibodies, humanized antibodies, chimeric antibodies and antigen-binding fragments of the foregoing) that bind a CXCR3 protein. For example, a nucleic acid (e.g., DNA) encoding an antibody of the invention can be incorporated into a suitable construct (e.g., an expression vector (e.g., a pLKTOK59 vector)) for further manipulation or for production of the encoded polypeptide in suitable host cells.

Expression constructs or expression vectors suitable for the expression of an antibody or antigen-binding fragment that binds a CXCR3 protein are also provided. For example, a nucleic acid encoding all or part of a desired antibody can be inserted into a nucleic acid vector, such as a plasmid or virus, for expression. The vector can be capable of replication in a suitable biological system (e.g., a replicon). A variety of suitable vectors are known in the art, including vectors which are maintained in single copy or multiple copies, or which become integrated into the host cell chromosome.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal or leader sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for prokaryotic (e.g., lac, tac, T3, T7 promoters for *E. coli*) and eukaryotic (e.g., simian virus 40 early or late promoter, Rous sarcoma virus long terminal repeat promoter, cytomegalovirus promoter, adenovirus late promoter, EF-1a promoter) hosts are available.

In addition, expression vectors typically comprise a selectable marker for selection of host cells carrying the vector, and, in the case of a replicable expression vector, an origin or replication. Genes encoding products which confer antibiotic or drug resistance are common selectable markers and may be used in prokaryotic (e.g., β-lactamase gene (ampicillin resistance), Tet gene for tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

Suitable expression vectors for expression in mammalian cells include, for example, pCDM8, pCDNA1.1/amp, pcDNA3.1, pRc/RSV, pEF-1 (Invitrogen Life Technologies, Carlsbad, Calif.), pCMV-SCRTPT®, pFB, pSG5, pXT1 (Stratagene, La Jolla, Calif.), pCDEF3 (Goldman, L.A., et al., *Biotechniques*, 21:1013-1015 (1996)), pSVSPORT (GIBCO division of Invitrogen Life Technologies, Carlsbad, Calif.), pEF-Bos (Mizushima, S., et al., *Nucleic Acids Res.*, 18:5322 (1990)) and the like. Expression vectors which are suitable for use in various expression hosts, such as prokaryotic cells (*E. coli*), insect cells (*Drosophila* Schnieder S2 cells, Sf9) and yeast (*P. methanolica, P. pasroris, S. cerevisiae*) are also available.

Thus, the invention provides an expression vector comprising a nucleic acid encoding an antibody, antigen-binding fragment of an antibody (e.g., a human, humanized, chimeric antibody or antigen-binding fragment of any of the foregoing), antibody chain (e.g., heavy chain, light chain) or antigen-binding portion of an antibody chain that binds a CXCR3 protein.

Recombinant Host Cells and Methods of Production

In another aspect, the invention relates to recombinant host cells and a method of preparing an antibody or antigen-binding fragment, antibody chain (e.g., heavy chain, light chain) or antigen-binding portion of an antibody chain, or fusion protein of the invention. As used herein, "recombinant host cell" and "host cell" do not include a recombinant cell that is part of a transgenic human or isolated from a transgenic human. The antibody or antigen-binding fragment can be obtained, for example, by the expression of one or more recombinant nucleic acids, encoding an antibody, antigen-binding fragment of an antibody, antibody chain or antigen-binding portion of an antibody chain that binds a CXCR3 protein, in a suitable host cell, or using other suitable methods. For example, the expression constructs described herein can be introduced into a suitable host cell, and the resulting cell can be maintained (e.g., in culture, in an animal, in a plant) under conditions suitable for expression of the constructs. Suitable host cells can be prokaryotic, including bacterial cells such as *E. coli, B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096), 293 (ATCC Accession No. CRL-1573), HeLa (ATCC Accession No. CCL-2), CVI (ATCC Accession No. CCL-70), WOP (Dailey, L., et al., *J. Virol.*, 54:739-749 (1985), 3T3, 293T (Pear, W. S., et al., *Proc. Natl. Acad. Sci. U.S.A.*, 90:8392-8396 (1993)) NSO cells, SP2/0, HuT 78 cells and the like, or plants (e.g., tobacco). (See, for example, Ausubel, F. M. et al., eds. *Current Protocols in Molecular Biology*, Greene Publishing Associates and John Wiley & Sons Inc. (1993).)

The invention also relates to a recombinant host cell which comprises a (one or more) recombinant nucleic acid or expression construct comprising a nucleic acid encoding an antibody, antigen-binding fragment of an antibody (e.g., a human, humanized, chimeric antibody or antigen-binding fragment of any of the foregoing), antibody chain (e.g., heavy chain, light chain), antigen-binding portion of an antibody chain that binds a CXCR3 protein or fusion protein. In particular embodiments, the recombinant host cell is hybridoma 5H7, hybridoma 7H5.

The invention also includes a method of preparing an antibody, antigen-binding fragment of an antibody (e.g., a human, humanized, chimeric antibody or antigen-binding fragment of any of the foregoing), antibody chain (e.g., heavy chain, light chain), antigen-binding portion of an antibody chain that binds a CXCR3 protein, or fusion protein, comprising maintaining a recombinant host cell of the invention under conditions appropriate for expression of an antibody, antigen-binding fragment of an antibody, antibody chain or antigen-binding fragment of an antibody chain. The method can further comprise the step of isolating or recovering the antibody, antigen-binding fragment of an antibody, antibody chain or antigen-binding fragment of an antibody chain, if desired.

For example, a nucleic acid molecule (i.e., one or more nucleic acid molecules) encoding the heavy and light chains of a human antibody that binds a CXCR3 protein, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. If desired, the encoded protein can be isolated or recovered (e.g., from the animal, the host cell, medium, milk). This process encompasses expression in a host cell of a transgenic non-human animal (see, e.g., WO 92/03918, GenPharm International) or plant.

The antibodies, antigen-binding fragments, antibody chains and antigen-binding portions thereof described herein also can be produced in a suitable in vitro expression system, by chemical synthesis or by any other suitable method.

Diagnostic and Therapeutic Methods

The antibodies (including antigen-binding fragments), immunoglobulin chains (including antigen-binding portions), fusion proteins and immuno-conjugates described herein can bind a CXCR3 protein and can be used to detect, measure, select, isolate and/or purify a CXCR3 protein or variants thereof (e.g., by affinity purification or other suitable methods), and to study CXCR3 protein structure (e.g., conformation) and function. The antibodies, immunoglobulin chains, fusion proteins and immuno-conjugates of the present invention also can be used in diagnostic applications (e.g., in vitro, ex vivo) and/or in therapeutic applications.

The antibodies (including antigen-binding fragments), immunoglobulin chains (including antigen-binding portions), fusion proteins and immuno-conjugates can be used to detect and/or measure the level of a CXCR3 protein in a sample (e.g., tissue or body fluid, such as an inflammatory exudate, bronchial lavage, blood, serum, bowel fluid, biopsy). In one example, a sample (e.g., tissue and/or body fluid) can be obtained from an individual and a suitable immunological method can be used to detect and/or measure CXCR3 protein expression. Suitable immunological methods for detecting or measuring CXCR3 protein expression include enzyme-linked immunosorbent assays (ELISA), radioimmunoassay, immunohistology, flow cytometry, and the like.

In one embodiment, the invention is a method of detecting or measuring a CXCR3 protein in a sample (e.g., a biological sample) comprising contacting a sample (e.g., a biological sample) with an antibody or antigen-binding fragment thereof that binds a CXCR3 protein under conditions suitable for binding of the antibody or antigen-binding fragment to the CXCR3 protein and detecting and/or measuring binding of the antibody or antigen-binding fragment to the CXCR3 protein. Binding of the antibody or antigen-binding fragment thereof to the CXCR3 protein indicates the presence of the CXCR3 protein in the sample. In an application of the method, an antibody or antigen-binding fragment of the invention can be used to analyze normal versus inflamed tissues (e.g., from a human) for CXCR3 protein reactivity and/or expression to detect associations between disease (e.g., inflammatory bowel disease, graft rejection) and increased expression of a CXCR3 protein (e.g., in affected tissues). In embodiments where the antibody or antigen-binding fragment binds a CXCR3 protein, the antibodies, antigen-binding fragments, fusion proteins and immuno-conjugates of the invention can be used to detect, measure, select, isolate and/or purify a CXCR3 protein or a cell expressing a CXCR3 protein.

The antibodies (including antigen-binding fragments), immunoglobulin chains (including antigen-binding portions), fusion proteins and immuno-conjugates of the present invention permit assessment of the presence of a CXCR3 protein in normal versus inflamed tissues, through which the presence or severity of disease, disease progress and/or the efficacy of therapy can be assessed. For example, therapy can be monitored and efficacy assessed. In one example, a CXCR3 protein can be detected and/or measured in a first sample obtained from a subject having an inflammatory disease and therapy can be initiated. Later, a second sample can be obtained from the subject and CXCR3 protein in the sample can be detected and/or measured. A decrease in the quantity of CXCR3 protein detected or measured in the second sample can be indicative of therapeutic efficacy.

The antibodies (including antigen-binding fragments), immunoglobulin chains (including antigen-binding portions), fusion proteins and immuno-conjugates described herein can modulate an activity or function of a CXCR3 protein, such as ligand binding (e.g., binding of IP-10, MIG or I-TAC) and/or leukocyte infiltration function, including recruitment and/or accumulation of leukocytes (e.g., T cells, NK cells, eosinophils) in tissues. Antibodies, immunoglobulin chains, fusion proteins and immuno-conjugates that bind an epitope can be used to selectively target cells expressing a CXCR3 protein for therapy. For example, an antibody that binds an epitope on a CXCR3 protein and is capable of activating complement (e.g., a human IgG1 antibody) can be administered to selectively deplete cells expressing a CXCR3 protein through, for example, complement-mediated lysis.

Preferably the antibodies (including antigen-binding fragments), immunoglobulin chains (including antigen-binding portions), fusion proteins and immuno-conjugates can selectively bind a CXCR3 protein and inhibit one or more CXCR3-mediated functions, such as CXCR3-mediated signal transduction, intracellular calcium release (calcium flux), chemotaxis, cell differentiation, cell proliferation or cell activation. In particularly preferred embodiments, the antibodies, immunoglobulin chains, fusion proteins and immuno-conjugates can inhibit the interaction of a CXCR3 protein with one or more of IP-10, MIG and I-TAC.

The antibodies (including antigen-binding fragments), immunoglobulin chains (including antigen-binding portions), fusion proteins and immuno-conjugates described herein can be administered to a subject to modulate an inflammatory response or to treat an inflammatory disease or disorder. For example, an antibody which inhibits the binding of a CXCR3 protein to a ligand (i.e., one or more ligands) can be administered in the treatment of diseases associated with leukocyte (e.g., lymphocyte, T helper-1 (Th1) lymphocyte, NK cell, eosinophil) infiltration of tissues, e.g., of mucosal tissues. An effective amount of an antibody, fusion protein and/or immuno-conjugate (i.e., one or more) can be administered to a subject (e.g., a mammal, such as a human or other primate) in order to treat such a disease. For example, inflammatory diseases, including (e.g., a disease or condition mediated by a cell expressing CXCR3 (e.g., a T helper-1 lymphocyte, an eosinophil), a mucosal inflammatory disease (e.g., inflammatory bowel disease (e.g., ulcerative colitis, Crohn's disease)), an autoimmune disease (e.g. rheumatoid arthritis, juvenile rheumatoid arthritis, multiple sclerosis, Graves' disease, diabetes), cancer (e.g. lymphoproliferative diseases), or an inflammatory disease precipitated by foreign matter (e.g. graft rejection (e.g., allograft rejection, xenograft rejection, graft-versus-host disease), response to bacterial or viral infection, a respiratory inflammatory disease (e.g. chronic obstructive pulmonary disease)) can be treated according to the present invention.

According to the method, the severity of symptoms associated with an inflammatory condition can be inhibited (reduced) in whole or in part. When the subject has a relapsing or chronic condition, an effective amount of an antibody, fusion protein and/or immuno-conjugate of the invention can be administered to treat the subject, and therapy can be continued (maintenance therapy) with the same or different dosing as indicated, to inhibit relapse or renewed onset of symptoms. Preferably, the antibodies, fusion proteins and/or immuno-conjugates are administered to treat a subject having an inflammatory disease, such as an inflammatory disease of the respiratory tract (e.g. bronchus, lung), of the nervous system (e.g., in microglia, astrocytes, in the cerebrospinal fluid), of the musculoskeletal system (e.g., in the joint) or of the alimentary canal and associated organs and tissues (e.g. mouth, salivary glands, small intestine, colon, pancreas, liver), to treat a subject rejecting an allograft or to treat a subject having a cancer (e.g., of lymphocytic origin).

In a preferred embodiment, the subject to be treated has an inflammatory bowel disease (IBD), such as ulcerative colitis, Crohn's disease, ileitis, Celiac disease, nontropical Sprue, enteropathy associated with seronegative arthropathies, colitis (e.g., microscopic or collagenous colitis), gastroenteritis (e.g., eosinophilic gastroenteritis), or pouchitis resulting after proctocolectomy and ileoanal anastomosis. In another preferred embodiment, the subject to be treated has an autoimmune disease affecting the nervous system (e.g., multiple sclerosis). In another preferred embodiment, the subject to be treated has a musculoskeletal inflammatory disease, such as rheumatoid arthritis.

In another embodiment, the subject to be treated has a pulmonary inflammatory disease, such as a chronic obstructive lung disease (e.g., chronic bronchitis, asthma, silicosis, chronic obstructive pulmonary disease), hypersensitivity pneumonitis, pulmonary fibrosis (e.g., idiopathic pulmonary fibrosis) or sarcoidosis. Subjects having pancreatitis or insulin-dependent diabetes mellitus, Sjogren's syndrome or Behcet's syndrome can also be treated using the present method. In other embodiments, the subject to be treated has an oral inflammatory disease (e.g., periodontitis) or a skin inflammatory disease (e.g., psoriasis). In other embodiments, the subject to be treated has a chronic inflammatory disease, such as resulting from a bacterial or viral infection (e.g., tuberculosis or hepatitis C). In other embodiments, the subject to be treated has a cancer, such as a lymphoproliferative disease (e.g., B cell chronic lymphocytic leukemia, mucosa-associtated lymphoid tissue type lymphoma, multiple myeloma, lymphoproliferative disease of granular lymphocytes).

In another embodiment, the invention is a method of inhibiting graft rejection (e.g., allograft rejection, xenograft rejection) or graft versus host disease, comprising administering to a subject in need thereof an effective amount of an antibody, fusion protein and/or immuno-conjugate of the invention. In particular embodiments, the transplanted graft is a cardiac or coronary tissue, a lung, a kidney, bone marrow tissue and the like.

As used herein, "subject" refers to humans and animals such as mammals, including, primates, cows, sheep, goats, horses, dogs, cats, rabbits, guinea pigs, rats, mice or other bovine, ovine, equine, canine, feline, rodent or murine species.

Diseases and conditions associated with inflammation, infection, and cancer can be treated using the method. In a preferred embodiment, the disease or condition is one in which the actions of cells bearing a CXCR3 protein, such as lymphocytes (e.g., activated or stimulated T lymphocytes, NK cells) and/or eosinophils, are to be inhibited or promoted for therapeutic or prophylactic purposes.

Diseases or conditions, including chronic diseases, of humans or other species which can be treated with the antibodies, fusion proteins and/or immuno-conjugates of the invention, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, celiac disease, ileitis and enteritis; sarcoidosis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, autoimmune thyroiditis, Behcet's syndrome, Sydenham's chorea, autoimmune autonomic neuropathy;

graft rejection (e.g., in transplantation), including allograft rejection, xenograft rejection or graft-versus-host disease;

viral infection, e.g., infection by hepatitis C virus (HCV), human papilloma virus (HPV), respiratory syncytial virus, influenza virus, simian immunodeficiency virus (SIV) or human immunodeficiency virus (HIV);

cancers and/or neoplastic diseases, such as leukemias and lymphomas;

other diseases or conditions in which undesirable inflammatory responses are to be inhibited can be treated, including, but not limited to, atherosclerosis (e.g., transplant accelerated atherosclerosis), restenosis, cytokine-induced toxicity, myositis (including polymyositis, dermatomyositis).

Modes of Administration

According to the method, an (i.e., one or more) antibody, antigen-binding fragment thereof, immunoglobulin heavy chain, antigen-binding portion thereof, immunoglobulin light chain, antigen-binding portion thereof, fusion protein and/or immuno-conjugate can be administered to the subject by an appropriate route, either alone or in combination with another drug. An "effective amount" of antibody, antigen-binding fragment thereof, immunoglobulin heavy chain, antigen-binding portion thereof, immunoglobulin light chain, antigen-binding portion thereof, fusion protein and/or immuno-conjugate is administered. An "effective amount" is an amount sufficient to achieve the desired therapeutic or prophylactic effect, under the conditions of administration, such as an amount sufficient to inhibit binding of CXCR3 protein to a ligand, e.g., IP-10, MIG or I-TAC, and thereby, inhibit CXCR3-mediated function, such as signal transduction, intracellular calcium release, chemotaxis, cell differentiation, cell proliferation or cell activation. The antibody, antigen-binding fragment thereof, immunoglobulin heavy chain, antigen-binding portion thereof, immunoglobulin light chain, antigen-binding portion thereof, fusion protein and/or immuno-conjugate can be administered in a single dose or multiple doses. Administration of the antibody, antigen-binding fragment thereof, immunoglobulin heavy chain, antigen-binding portion thereof, immunoglobulin light chain, antigen-binding portion thereof, fusion protein and/or immuno-conjugate can occur daily, weekly, biweekly or monthly, preferably weekly, biweekly or monthly. Administration of the antibody, antigen-binding fragment thereof, immunoglobulin heavy chain, antigen-binding portion thereof, immunoglobulin light chain, antigen-binding portion thereof, fusion protein and/or immuno-conjugate also can occur every other month or every three months. The antibody, antigen-binding fragment thereof, immunoglobulin heavy chain, antigen-binding portion thereof, immunoglobulin light chain, antigen-binding portion thereof, fusion protein and/or immuno-conjugate can be administered as a bolus and/or infusion (e.g., continuous infusion). The dosage can be determined by methods known in the art and is dependent, for example, upon the antibody, antigen-binding fragment, fusion protein and/or immuno-conjugate chosen, the subject's age, sensitivity and tolerance to drugs, and overall well-being. Typically, an effective amount can range from about 1 or 10 mg per administration to about 800, 1000, 1500 or 2000 mg per administration for an adult. Preferably, the dosage ranges from about 10, 20, 30 or 50 mg per administration to about 700 or 1000 mg per administration. For example, an effective amount of a human, humanized or chimeric antibody per administration (or antigen-binding fragment of any of the foregoing) can range from about 0.01 mg/kg to about 5, 10, 15 or 20 mg/kg, preferably in the range of about 3, 5, 7, 10 or 15 mg/kg. Human, humanized and chimeric antibodies can often be administered with less frequency than other types of therapeutics.

A variety of routes of administration are possible including, for example, oral, dietary, topical, transdermal, rectal, parenteral (e.g., intravenous, intraarterial, intramuscular, subcutaneous, intradermal, intraperatoneal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the agent chosen, and the condition (e.g., disease) being treated, however, oral or parenteral administration is generally preferred.

The antibody, antigen-binding fragment thereof, immunoglobulin heavy chain, antigen-binding portion thereof, immunoglobulin light chain, antigen-binding portion thereof, fusion protein and/or immuno-conjugate and any other therapeutic agent to be administered can be administered as a neutral compound or as a salt. Salts of compounds (e.g., an antibody) containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counter-anion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The antibody, antigen-binding fragment thereof, immunoglobulin heavy chain, antigen-binding portion thereof, immunoglobulin light chain, antigen-binding portion thereof, fusion protein and/or immuno-conjugate can be administered to the individual as part of a pharmaceutical composition, for example, for modulation (e.g., inhibition) of CXCR3 function (e.g., ligand binding and/or signal transduction, intracellular calcium release, chemotaxis, cell differentiation, cell proliferation or cell activation), or treating a subject having a disease described herein. The pharmaceutical composition can comprise an antibody, antigen-binding fragment, fusion protein and/or immuno-conjugate of the invention and a pharmaceutically or physiologically acceptable carrier. In another embodiment, the pharmaceutical composition can comprise an immuglobulin heavy chain or antigen-binding portion thereof and a physiologically acceptable carrier. The foregoing composition can further comprise a complementary light chain or antigen-binding portion thereof. In another embodiment, the pharmaceutical composition can comprise an immunoglobulin light chain or antigen-binding portion thereof and a physiologically acceptable carrier. The foregoing composition can further comprise a complementary heavy chain or antigen-binding portion thereof. Formulation will vary according to the route of administration selected (e.g., solution, emulsion, capsule). Suitable pharmaceutical and physiological carriers can contain inert ingredients which do not interact with the antibody, fusion protein and/or immuno-conjugate. Standard pharmaceutical formulation techniques can be employed, such as those described in *Remington's Pharmaceutical Sciences*, Mack Publishing Company, Easton, Pa. Suitable pharmaceutical carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, the antibody, antigen-binding fragment thereof, immunoglobulin heavy chain, antigen-binding portion thereof, immunoglobulin light chain, antigen-binding portion thereof, or fusion protein of the invention and other therapeutic agents that are proteins can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The present invention will now be illustrated by the following Examples, which are not intended to be limiting in any way.

EXAMPLES

Example 1

Generation of Human Antibodies Which Bind Human CXCR3

XENOMOUSE® Technology mice (genetically engineered mice with human antibody genes from Abgenix Inc., Fremont, Calif.) were immunized with transfected L1.2 (murine B lymphoma cell line) cells which expressed high levels of CXCR3 receptor (CXCR3 transfectants). The production of these cells was described in U.S. Pat. No. 6,184,358 B1, the contents of which are incorporated herein by reference in their entirety. The mice were immunized multiple times with CXCR3 transfectants using the protocol presented Table 3.

TABLE 3

Immunization Protocol

| Time | |
|---|---|
| Day 1, Week 0 | IP, mito |
| Week 2 | IP, mito |
| Week 4 | IP, mito |
| Week 7.5 | IP, mito |
| Week 9 | IP |
| Week 11 | IP, CFA |
| Week 13 | IP, CFA |
| Week 15 | IP |
| Week 30.5 | IP |
| Week 32.5 | IV |

IP, mito = intraperitoneal injection of 0.2-0.3 ml phosphate-buffered saline (PBS) containing $1 \times 10^7$ CXCR3 transfectants which had been treated with 25 µg/ml mitomycin C for 30 min
IP = intraperitoneal injection of 0.2-0.3 ml PBS containing $1 \times 10^7$ CXCR3 transfectants
CFA = Complete Freund's Adjuvant included in injection
IV = intravascular injection of $0.33 \times 10^7$ CXCR3 transfectants in 0.1 ml PBS Three days after the last immunization, five animals were sacrificed, their spleen cells were isolated, combined and used to produce hybridomas by standard methods. About $3 \times 10^8$ spleen cells were fused with 5- to 10-fold fewer SP2/0-Ag14 fusion partner cells (ATCC, No. CRL-1581, Manassas, Va.) or P3X63Ag8.653 fusion partner cells (ATCC, No. CRL-1580, Manassas, Va.), by brief resuspension in polyethylene glycol 1500 (50% in 75 mM HEPES, Boehringer-Mannheim, now Roche Applied Science, Indianapolis, Ind.), to generate the hybridomas. After fusion, the cells were selected by incubation for two weeks in hypoxanthine, aminopterin, thymidine (HAT) medium specificity was assessed by staining CXCR3 transfectants, control L1.2 cells and L1.2 cells that expressed human CCR1, CCR2, CCR3, CCR4, CCR5, CXCR1, CXCR2, or CXCR4 (Qin et al. (1998) *J. Clin. Invest.* 101:746-54). The binding of antibody from the hybridoma supernatants to receptor transfectants was detected by phycoerythrin-conjugated anti-human IgG with analysis by flow cytometry. Positive wells were those that contained supernatant which stained the CXCR3 transfectants, but not L1.2 cells which expressed the other chemokine receptors tested. Positive wells were subcloned to yield hybridoma cell lines. Hybridoma cultures were maintained in DMEM with 10% fetal calf serum, 10 units/ml interleukin-6, 0.1% L-glutamine, and 0.1% penicillin/streptomycin. Isotype determination was performed using secondary antibodies purchased from The Binding Site (Birmingham, UK) and revealed that both human mAb 5H7 and human mAb 7H5 are of the IgG2, kappa isotype.

Example 2

Characterization of Antibody Binding

The cell-type specificities and affinities of human mAb 5H7 and human mAb 7H5 antibodies were characterized. For the studies described in the following paragraphs, the human mAb 5H7 or human mAb 7H5 antibodies were biotinylated for detection by phycoerythrin conjugated to streptavidin (streptavidin-PE). The lymphocyte populations from normal donors were discriminated by gating with forward and side scatters. The mouse anti-CXCR3 mAb 1C6 was used as a positive control.

The results revealed that a subpopulation of lymphocytes, but not monocytes or granulocytes, were detected by human mAb 5H7. In a study using Cy5-conjugated anti-CD3, FITC-conjugated anti-CD4 and anti-CD8 to stain total T cells or subsets of T cells, respectively, and CD19 to identify B cells, the staining pattern of human mAb 5H7 was similar to that of murine mAb 1C6 (Qin et al. (1998) *J. Clin. Invest.* 101:746-54).

In another study, normal blood lymphocytes were cultured in the presence of IL-2 (20 U/ml) for 14 days to activate T cells. These activated T cells were incubated with 2 µg/ml biotinylated human mAb 5H7 followed by streptavidin-PE. All the activated T cells were positively stained by human mAb 5H7, which is similar to the staining pattern of the mouse anti-human CXCR3 mAb 1C6.

The strength of human monoclonal antibody 5H7 and human monoclonal antibody 7H5 binding to CXCR3 was measured using CXCR3 transfecrants. The mean streptavidin-PE fluorescence detected when 10 µg/ml of each purified mAb was used to stain CXCR3 transfectants was used as 100% fluorescence. The mean fluorescence intensity detected at several antibody concentrations (indicated in FIG. 1) were plotted, and the concentration of antibody which produced 50% fluorescence (EC50) was calculated using KALEIDAGRAPHYM™ data analysis software (Synergy Software, Reading, Pa.). The calculated EC50values are 0.5 nM, 1.2 nM and 2.3 nM for human mAb 5H7, human mAb 7H5 and mouse mAb 1C6, respectively (FIG. 1).

Example 3

Human Monoclonal Antibodies 5H7 and 7H5 Inhibit CXCR3-Mediated Chemotaxis

Inhibition of CXCR3-mediated chemotaxis by human mAb 5H7 and human mAb 7H5 was studied in an in vitro chemotaxis assay and compared to the inhibition by mouse mAb 1C6. CXCR3/L1.2 transfectants were used in the chemotaxis assays. Chemokines IP-10, MIG and I-TAC (PeproTech, Inc. Rocky Hill, N.J.) were diluted in RPMI/0.5% BSA to 5 nM in the bottom chamber of TRANSWELL® cell culture insert plates (Corning Incorporated Life Sciences, Acton, Mass.). About $1 \times 10^6$ transfectants were added to the top chamber without or with 100 µ/ml of purified antibody, and the plates were incubated at 37° C., 5%$CO_2$ for 4 hours. Cells which Migrated to the lower chamber were collected, suspended, and counted by flow cytometry for a set time of 30 seconds.

The results of chemotaxis assays using purified 5H7, 1C6 or 7H5 antibodies are presented in Table 4 and show that each antibody inhibited chemotaxis.

TABLE 4

Number of Cells Which Migrated to the Bottom Chamber in a Chemotaxis Assay

| | Ligand in Bottom Chamber | | |
|---|---|---|---|
| Top Chamber | IP-10 | MIG | I-TAC |
| Control, no antibodies | 4151 | 3402 | 11550 |
| 1C6 | 51 | 2346 | 7664 |
| 5H7, subclone 1 | 1235 | 1268 | 2676 |
| 5H7, subclone 2 | 486 | 836 | 1970 |
| 7H5, subclone 2 | 1252 | 1307 | 2526 |
| 7H5, subclone 4 | 2760 | 2197 | 7495 |
| No ligand in bottom | 0 | 0 | 0 |

Figure 2:
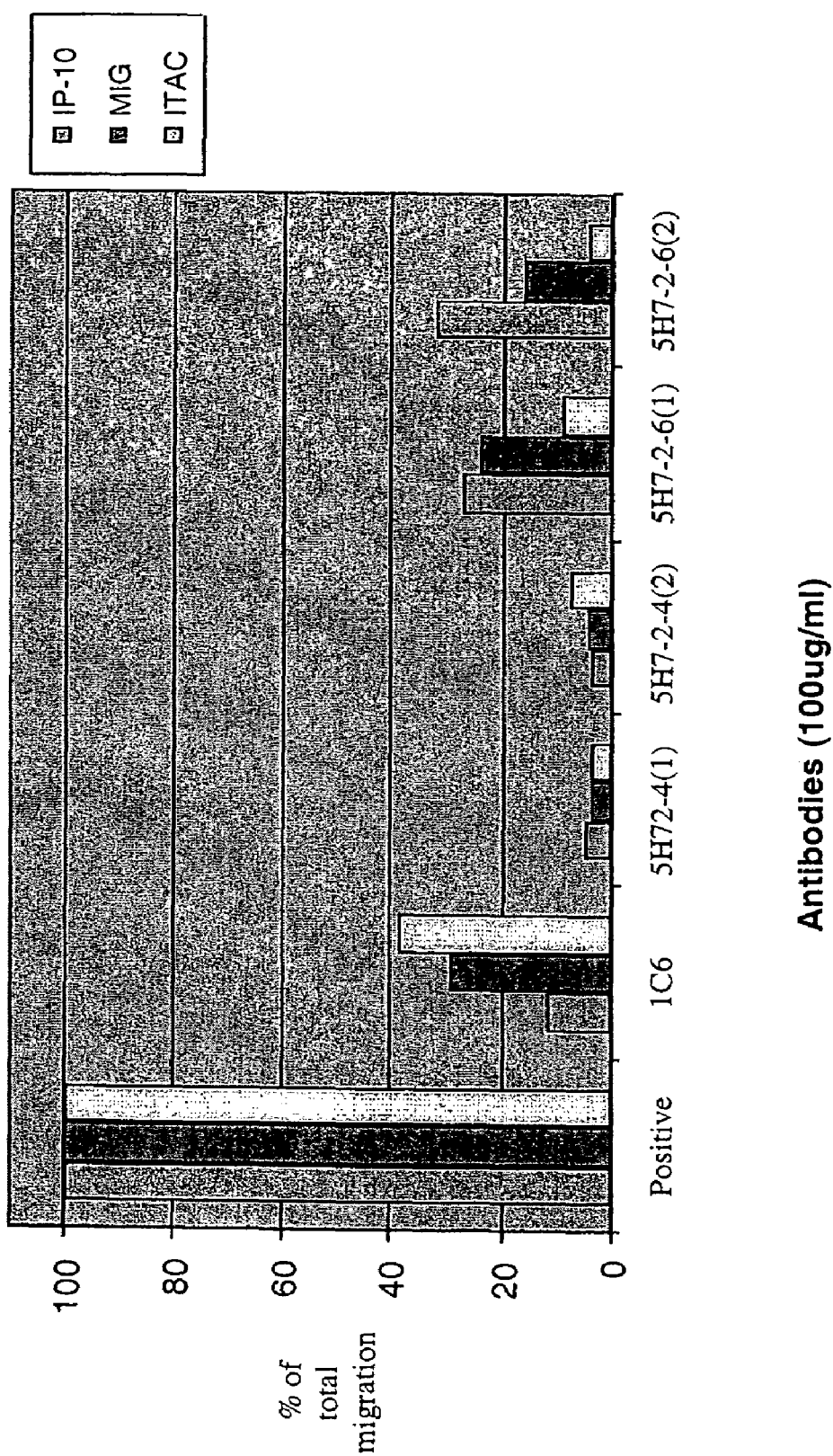
FIG. 2 is a histogram depicting the number of CXCR3 transfectants Migrating in an in vitro chemotaxis assay toward a ligand (IP-10, MIG or I-TAC) in the absence ("positive") or presence of a monoclonal antibody to human CXCR3 (murine monoclonal antibody 1C6, human monoclonal antibody 5H7, subclone 4, elution tubes (1) or (2) or human monoclonal antibody 5H7, subclone 6, elution tubes (1) or (2)). The results show that human monoclonal antibody 5H7 inhibits CXCR3-mediated chemotaxis in response to IP-10, MIG and I-TAC.

FIG. 2 shows the results of another study demonstrating that CXCR3-mediated chemotaxis induced by three ligands of CXCR3 (IP10, MIG and I-TAC) was inhibited by high amounts of purified antibodies from two subclones of human 5H7 hybridoma (subclones 2-4 and 2-6, fractions (1) and (2) of each) and from mouse 1C6 hybridoma.

Figure 3:
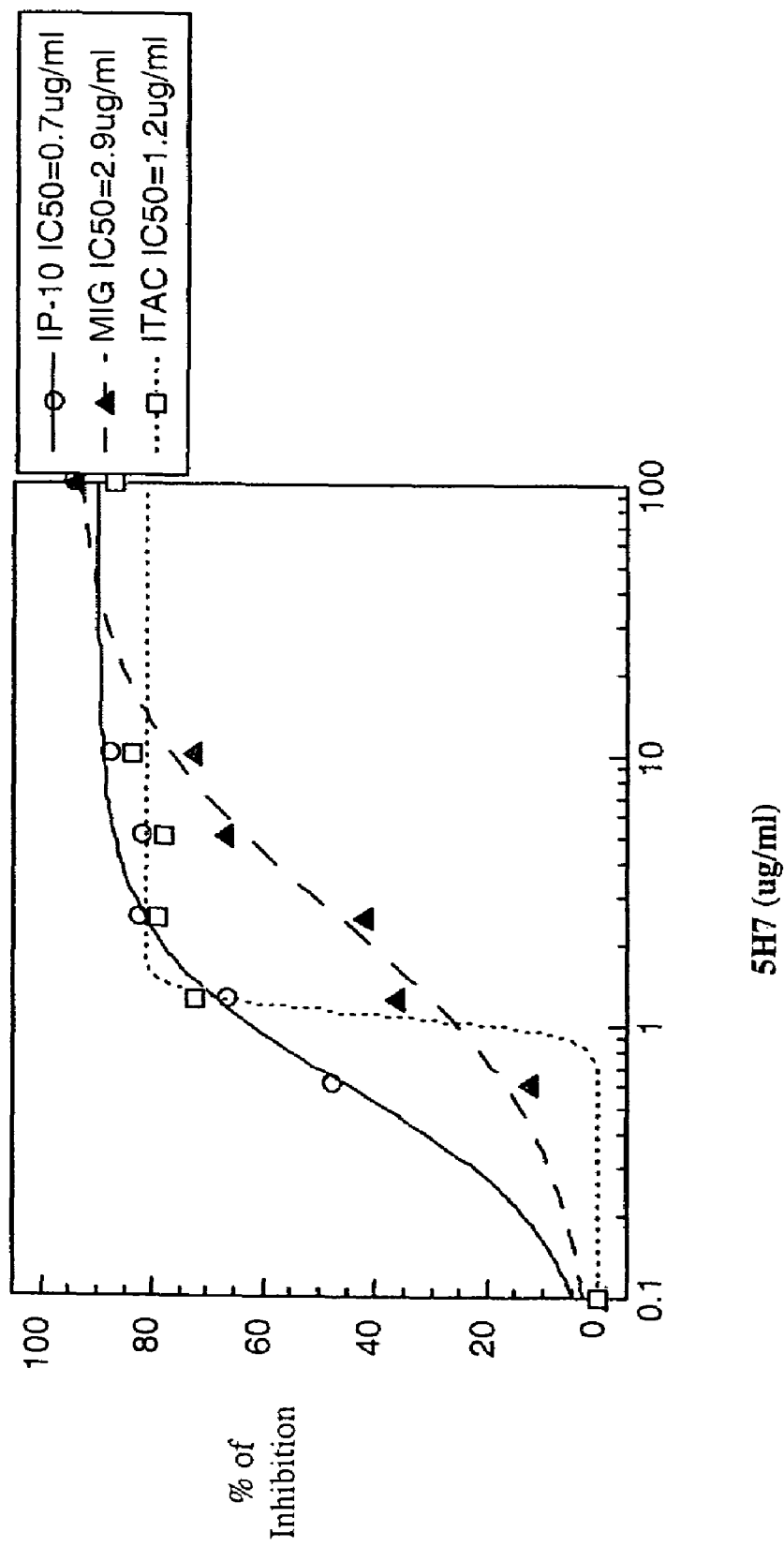
FIG. 3 is a graph showing the percent inhibition of chemotaxis of CXCR3 transfectants toward IP-10, MIG or I-TAC by human monoclonal antibody 5H7 in an in vitro chemotaxis assay. The IC50 of human mAb 5H7 against IP-10 is 0.7 μg/ml, against MIG is 2.9 μg/ml and against I-TAC is 1.2 μg/ml.
Figure 4:
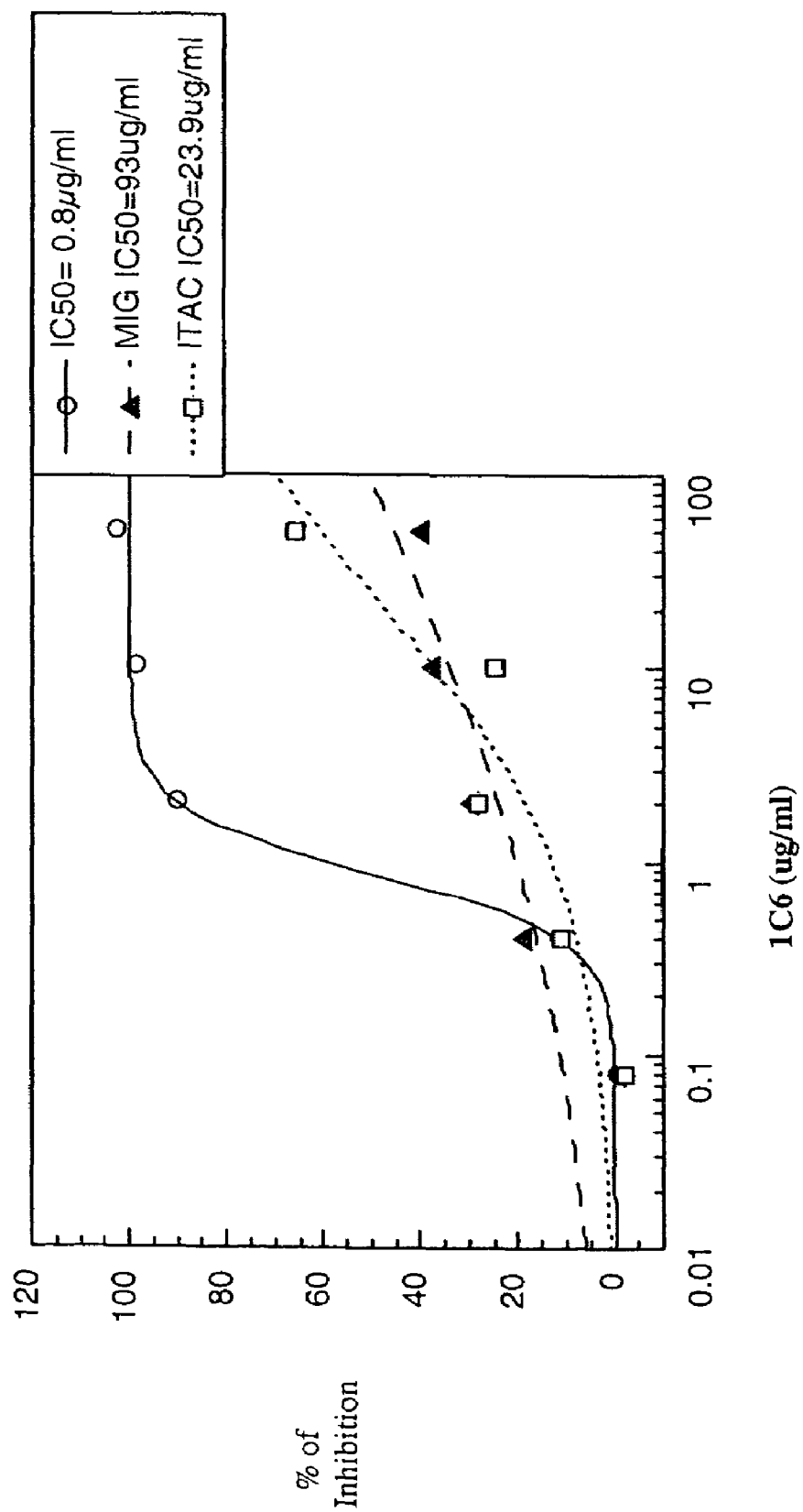
FIG. 4 is a graph showing the percent inhibition of chemotaxis of CXCR3 transfectants toward IP-10, MIG or I-TAC by murine monoclonal antibody 1C6 in an in vitro chemotaxis assay. The IC50 of murine mAb 1C6 against IP-10 is 0.8 μg/ml, against MIG is 93 μg/ml and against I-TAC is 23.9 μg/ml.

The abilities of human mAb 5H7 and murine mAb 1C6 to inhibit CXCR3-mediated chemotaxis induced by IP-10, MIG or I-TAC were quantified. Maximum chemotaxis was the number of cells which Migrated to the lower chamber (which contained IP-10, MIG or I-TAC) in the absence of any antibodies. Percent inhibition was calculated as follows: 100x[1−(s−b)/(t−b)], where s is the number of cells which Migrated to the lower chamber in test wells, b is the background Migration in the absence of chemokine, and t is the maximum chemotaxis. Different concentrations of antibody were included with CXCR3 transfectants in the top chamber and charnotaxis was assessed. The concentration of antibody which inhibited chemotaxis by 50% (IC50) was calculated using KALEWAGRAPH™ data analysis software (Synergy Software, Reading, Pa.). The inhibition profile for human mAb 5H7 is shown in FIG. 3 and for 1C6 is shown in FIG. 4. The IC50 of human mAb 5H7 against IP-10 is 0.7 µ/ml, against MIG is 2.9 µg/ml and against I-TAC is 1.2 µg/ml. The IC50 of murine mAb 1C6 against IP-10 is 0.8 µg/ml, against MIG is 93 µg/ml and against I-TAG is 24 µg/ml. At 50 µg/ml 1C6 inhibited about 40% of MIG- and 60% of I-TAC-induced CXCR3-medicated chemotaxis, respectively.

Example 4

Human mAbs 5H7 and 7H5 Are Not CXCR3 Agonists

Human T cells were activated by anti-CD3 mAb (OKT3, 3 µg/ml) for three days. Then they were expanded in the presence of IL-2 (2 mg/ml) for up to 4 weeks. Cells were loaded with Fluo-3 (Molecular Probes, Inc., Eugene, Oreg.) at 10 nM for 30 minutes at 37° C., washed once in buffer (Hank's Balanced Salt Solution supplemented with 0.1% BSA). The cells were resuspended in the buffer and stimulated with IP10, MIG, or I-TAC in the presence of purified human mAb 5H7, purified human mAb 7H5 or purified murine mAb 1C6. The changes in real time were recorded with FACS flow cytometry measuring fluorescence intensity of FLI vs. time. None of the mAbs tested elicited a noticeable intracellular Ca++ mobilization at 100 µg/ml of antibody concentration. The CXCR3 ligand I-TAC was used at 5 nM as the positive control to demonstrate intracellular Ca++ mobilization induced by chemokines. Other ligands, IP-10 and MIG induced similar responses at this concentration.

Example 5

Determination of the Primary Structure of Human mAb 5H7 and Human mAb 7H5

RNA was isolated from multiple subclones of 5H7 and 7H5 hybridomas. Transcribed heavy and light chain variable regions of hybridoma inununoglobulin genes were amplified by polymerase chain reaction (PCR) using an IG-PRIMER Set (immunoglobulin amplification reagents, Novagen, Inc., Madison, Wis.) having degenerate primers. A minilibrary was prepared from the amplified variable region cDNAs using the TOPO® Cloning kit (Invitrogen Life Technologies, Carlsbad, Calif.). All the minilibrary clones were sequenced to identify the sequences encoding the hybridoma heavy and light chains. Through aligning overlapping segments, the sequence of one active heavy chain and one active light chain was determined for each hybridoma.

Further confirmation of the human mAb 5H7 structure and function was achieved by inserting the sequences into an expression vector for transfection of non-hybridoma cells. Nucleic acid sequence encoding the variable regions (VH and VK) of human mAb 5H7 (SEQ ID NOs:1 and 9) were inserted in the pLKTOK59 vector. This vector can be used to express an antibody (heavy and light chains expression driven by the EF-1a promoter) that contains a human kappa constant region, and a human IgG1 constant region that contains mutations at positions L235A and G237A (IgG1-FcRmut). These mutations inhibit the binding of the constant region to human Fc receptors and inhibit the initiation of antibody-dependent cellular cytotoxicity reactions. The nucleic acid encoding the variable region of the immunoglobulin heavy chain (VH) of 5H7 and containing SEQ ID NO:1 was prepared by PCR using the following primers: TTACCCAATTGTGTCCT-GTCCCAGGTGCAGGTGGTGCAGTCTGGGGCTG (SEQ ID NO:38) and TGGAGGCTGAGCTGACGGTGAC-CGTGGTCCCTTGGCCCCAGACGTCCATA (SEQ ID NO:39). These contain restriction sites (an Mfe I restriction site in the leader sequence and the BIp I restriction site in the 3' end) which were used for in-frame insertion of the human mAb 5H7 VH nucleic acid sequence after the leader sequence of the heavy chain construct in the pLKTOK59D vector. The nucleic acid encoding the variable region of the immunoglobulin light chain (VK) of 5H7 and containing SEQ ID NO:9 was prepared by PCR using the following primers: TTC-CCAGGGTCCCGTTCCGACATCCAGAT-GACCCAGTCTCCATCCTCCCTG (SEQ ID NO:40), AGCCACCGTACGCTTAATCTCCAGTCGTGTCCCTTG (SEQ ID NO:41), CTGAACCTTGATGGGACTC-CACTTTGCAAACTGGATGCGCCATAGAT (SEQ ID NO:42), TCCAGTTTGCAAAGTGGAGTCCCAT-CAAGGTTCAGTGGCAGTGGATCTG (SEQ ID NO:43), and AGCCACCGTACGCTTAATCTCCAGTCGT-GTCCCTTGGCCGAAACTGATAGGGAC TCT-GAAACTCTGTTGACAGTAGTAAGTTG (SEQ ID NO:44). The first two and the last (SEQ ID NOs:40, 41 and 44) contain restriction sites (a PpuM I restriction site in the leader sequence and the BslW I restriction site in the 3' end) which were used for in-frame insertion of the human mAb 5H7 VK nucleic acid sequence after the leader sequence of the light chain construct in the pLKTOK59D vector. The resulting vector, named pLKTOK59D-5H7VHVK was transfected into 293T (transformed human renal epithelial line expressing two viral oncogenes, adenovirus E1a and SV40 large T antigen) cells. Conditioned culture medium was collected from these transient transfectants.

All documents cited throughout this application including references, pending patent applications and published patents, are hereby expressly incorporated herein by reference in their entirety.

Although preferred embodiments of the invention have been described using specific terms, such description are for illustrative purposes only, and it is to be understood that changes and variations may be made without departing from the spirit or scope of the invention. Those skilled in the art will recognize, or be able to ascertain using no more than routine experimentation, many equivalents of the specific embodiments of the invention described herein. Such equivalents are intended to be encompassed by the following claims.

What is claimed is:

1. An isolated antibody or antigen-binding fragment thereof, wherein the antibody or antigen-binding fragment thereof binds a CXCR3 protein and
said antibody or antigen-binding fragment comprises three heavy chain complementarity determining regions (HCDR1, HCDR2 and HCDR3) comprising the amino acid sequences:

| HCDR1: | SEQ ID NO: 4; |
| HCDR2: | SEQ ID NO: 6; and |
| HCDR3: | SEQ ID NO: 8; | three light chain complementarity determining regions (LCDR1, LCDR2 and LCDR3) comprising the amino acid sequences:

| LCDR1 | SEQ ID NO: 12; |
| LCDR2 | SEQ ID NO: 14; and |
| LCDR3 | SEQ ID NO: 16. |

2. The antibody or antigen-binding fragment of claim 1, wherein said antibody or antigen-binding fragment thereof:
inhibits binding of a ligand to said CXCR3 protein;
inhibits a function of a CXCR3 protein selected from the group consisting of CXCR3 ligand-induced intracellular calcium release, CXCR3 ligand-induced chemotaxis, CXCR3 ligand-induced cell differentiation, CXCR3 ligand-induced cell proliferation and CXCR3 ligand-induced cell activation;
competitively inhibits binding of human monoclonal antibody 5H7 to said CXCR3 protein; or has the epitopic specificity of human monoclonal antibody 5H7.

3. The antibody or antigen-binding fragment of claim 2 wherein said CXCR3 ligand is selected from the group consisting of IP-10, MIG and I-TAC.

4. The antibody or antigen-binding fragment thereof of claim 1 wherein said antibody or antigen-binding fragment thereof is selected from the group consisting of a human antibody, an antigen-binding fragment of a human antibody, a humanized antibody, an antigen-binding fragment of a humanized antibody, a chimeric antibody and an antigen-binding fragment of a chimeric antibody.

5. The antibody or antigen-binding fragment thereof of claim 1, wherein said antibody or antigen-binding fragment is an antigen-binding fragment selected from the group consisting of an Fab fragment, an Fab' fragment, an F(ab')$_2$ fragment and an Fv fragment.

6. An isolated antibody or antigen-binding fragment thereof that binds a CXCR3 protein and comprises a heavy chain variable region and a light chain variable region, wherein the heavy chain variable region is encoded by SEQ ID NO:1, and
the light chain variable region is encoded by SEQ ID NO:9.

7. An isolated antibody or antigen-binding fragment thereof that binds a CXCR3 protein and comprises a heavy chain variable region and a light chain variable region, wherein the heavy chain variable region comprises SEQ ID NO:2, and
the light chain variable region comprises SEQ ID NO:10.

8. The antibody produced by hybridoma 5H7 (ATCC® Accession No. PTA-5388).

9. The 5H7 (ATCC® Accession No. PTA-5388) hybridoma.

10. An isolated antibody, wherein the heavy chain comprises the immunoglobulin heavy chain of the antibody produced by hybridoma 5H7(ATCC® Accession No. PTA-5388), wherein the antibody binds a CXCR3 protein.

11. An isolated antibody, wherein the light chain comprises the immunoglobulin light chain of the antibody produced by hybridoma 5H7 (ATCC® Accession No. PTA-5388), wherein the antibody binds a CXCR3 protein.

12. A composition comprising the antibody or antigen-binding fragment of claim 1 and a physiologically acceptable carrier.

13. The antibody or antigen-binding fragment thereof of claim 1 wherein the antibody or antigen-binding fragment thereof comprises a heavy chain or antigen-binding portion thereof comprising a variable region comprising SEQ ID NO:2.

14. The antibody or antigen-binding fragment thereof of claim 1 wherein the antibody or antigen-binding fragment thereof comprises a light chain or antigen-binding portion thereof comprising a variable region comprising SEQ ID NO:10.

15. An antigen binding fragment of the antibody of claim 8.

16. An antigen binding fragment of the antibody of claim 10.

17. An antigen binding fragment of the antibody of claim 11.

* * * * *

SEQUENCE LISTING

<160> NUMBER OF SEQ ID NOS: 44

<210> SEQ ID NO 1
<211> LENGTH: 378
<212> TYPE: DNA
<213> ORGANISM: Homo sapiens

<400> SEQUENCE: 1
caggtgcagg tggtgcagtc tggggctgag gtgaagaagc ctggggcctc agtgaaggtc      60
tcctgcaaga cttctggata caccttcacc ggcaactata tacactgggt gcgacaggcc     120
cctggacaag gcttgagtg atgggatgg atcaaccctaacagtggtgg cacaaacttt        180 gcacagaagt ttcagggcag gtcaccatg accagggaca cgtccatcac cacagcctac     240
atggtcctga gcaggctgag atctgacgac acggccgtgt attactgtgc gagagggggg     300
aataacatga tagtggtggc cagaggctac tacggtatgg acgtctgggg ccaagggacc     360
acggtcaccg tcagctca                                                   378

<210> SEQ ID NO 2
<211> LENGTH: 126
<212> TYPE: PRT
<213> ORGANISM: Homo sapiens
<220> FEATURE:
<221> NAME/KEY: SITE
<222> LOCATION: (31)...(35)
<223> OTHER INFORMATION: CDR1
<220> FEATURE:
<221> NAME/KEY: SITE
<222> LOCATION: (50)...(66)
<223> OTHER INFORMATION: CDR2
<220> FEATURE:
<221> NAME/KEY: SITE
<222> LOCATION: (99)...(115)
<223> OTHER INFORMATION: CDR3

<400> SEQUENCE: 2

Gln Val Gln Val Val Gln Ser Gly Ala Glu Val Lys Lys Pro Gly Ala
 1               5                  10                  15

Ser Val Lys Val Ser Cys Lys Thr Ser Gly Tyr Thr Phe Thr Gly Asn
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Phe Ala Gln Lys Phe
    50                  55                  60

Gln Gly Arg Val Thr Met Thr Arg Asp Thr Ser Ile Thr Thr Ala Tyr
65                  70                  75                  80

Met Val Leu Ser Arg Leu Arg Ser Asp Asp Thr Ala Val Tyr Tyr Cys
                85                  90                  95

Ala Arg Gly Gly Asn Asn Met Ile Val Val Ala Arg Gly Tyr Tyr Gly
            100                 105                 110

Met Asp Val Trp Gly Gln Gly Thr Thr Val Thr Val Ser Ser
        115                 120                 125

<210> SEQ ID NO 3
<211> LENGTH: 15
<212> TYPE: DNA
<213> ORGANISM: Homo sapiens

<400> SEQUENCE: 3
ggcaactata tacac                                                       15

```
<210> SEQ ID NO 4
<211> LENGTH: 5
<212> TYPE: PRT
<213> ORGANISM: Homo sapiens

<400> SEQUENCE: 4

Gly Asn Tyr Ile His
 1               5

<210> SEQ ID NO 5
<211> LENGTH: 51
<212> TYPE: DNA
<213> ORGANISM: Homo sapiens

<400> SEQUENCE: 5
tggatcaacc ctaacagtgg tggcacaaac tttgcacaga gtttcagggc                51

<210> SEQ ID NO 6
<211> LENGTH: 17
<212> TYPE: PRT
<213> ORGANISM: Homo sapiens

<400> SEQUENCE: 6

Trp Ile Asn Pro Asn Ser Gly Gly Thr Asn Phe Ala Gln Lys Phe Gln
 1               5                  10                  15

Gly

<210> SEQ ID NO 7
<211> LENGTH: 51
<212> TYPE: DNA
<213> ORGANISM: Homo sapiens

<400> SEQUENCE: 7 gggggaata acatgatagt ggtggccaga ggctactacg gtatggacgt c               51

<210> SEQ ID NO 8
<211> LENGTH: 17
<212> TYPE: PRT
<213> ORGANISM: Homo sapiens

<400> SEQUENCE: 8

Gly Gly Asn Asn Met Ile Val Val Ala Arg Gly Tyr Tyr Gly Met Asp
 1               5                  10                  15

Val

<210> SEQ ID NO 9
<211> LENGTH: 321
<212> TYPE: DNA
<213> ORGANISM: Homo sapiens

<400> SEQUENCE: 9
gacatccaga tgacccagtc tccatcctcc ctgtctgcat ctgtaggaga cagagtcacc     60
atcacttgcc gggcaagtca gagcattggc aggtacttaa attggtatca acagaaacca   120
gggaaagccc ctaaactcct gatctatggc gcatccagtt tgcaaagtgg agtcccatca   180
aggttcagtg gcagtggatc tgggacagaa ttcactctca ccatcagcag tctgcaacct   240
gaagattttg caacttacta ctgtcaacag agtttcagag tccctatcag tttcggccaa   300
gggacacgac tggagattaa g                                              321
```

<210> SEQ ID NO 10
<211> LENGTH: 107
<212> TYPE: PRT
<213> ORGANISM: Homo sapiens
<220> FEATURE:
<221> NAME/KEY: SITE
<222> LOCATION: (24)...(34)
<223> OTHER INFORMATION: CDR1
<220> FEATURE:
<221> NAME/KEY: SITE
<222> LOCATION: (50)...(56)
<223> OTHER INFORMATION: CDR2
<220> FEATURE:
<221> NAME/KEY: SITE
<222> LOCATION: (89)...(97)
<223> OTHER INFORMATION: CDR3

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Phe Arg Val Pro Ile
                85                  90                  95

Ser Phe Gly Gln Gly Thr Arg Leu Glu Ile Lys
            100                 105

<210> SEQ ID NO 11
<211> LENGTH: 33
<212> TYPE: DNA
<213> ORGANISM: Homo sapiens

<400> SEQUENCE: 11
cgggcaagtc agagcattgg caggtactta aat                                  33

<210> SEQ ID NO 12
<211> LENGTH: 11
<212> TYPE: PRT
<213> ORGANISM: Homo sapiens

<400> SEQUENCE: 12

Arg Ala Ser Gln Ser Ile Gly Arg Tyr Leu Asn
 1               5                  10

<210> SEQ ID NO 13
<211> LENGTH: 21
<212> TYPE: DNA
<213> ORGANISM: Homo sapiens

<400> SEQUENCE: 13
ggcgcatcca gtttgcaaag t                                               21

<210> SEQ ID NO 14
<211> LENGTH: 7
<212> TYPE: PRT
<213> ORGANISM: Homo sapiens

<400> SEQUENCE: 14

```
Gly Ala Ser Ser Leu Gln Ser
  1               5
```

<210> SEQ ID NO 15
<211> LENGTH: 27
<212> TYPE: DNA
<213> ORGANISM: Homo sapiens

<400> SEQUENCE: 15
caacagagtt tcagagtccc tatcagt                                          27

<210> SEQ ID NO 16
<211> LENGTH: 9
<212> TYPE: PRT
<213> ORGANISM: Homo sapiens

<400> SEQUENCE: 16

```
Gln Gln Ser Phe Arg Val Pro Ile Ser
  1               5
```

<210> SEQ ID NO 17
<211> LENGTH: 378
<212> TYPE: DNA
<213> ORGANISM: Homo sapiens

<400> SEQUENCE: 17
caggtgcaag tggtgcagtc tgggctgag gtgaagaagc ctggggcctc agtgaaggtc        60
tcctgcaagg cttctggata caccttcacc ggctactata tacactgggt gcgacaggcc     120
cctggacaag gcttgagtg gatgggatgg atcaaccctg acagtggtgg cacaaactat      180
gcacagaagt tcaggcag ggtcaccatg accaggaca cgtccatcag cacagcctac        240
atggtcctga caggctgag atctgacgac acggccgtat attactgtgc gaaggggggg     300
atcaatatga gtagtggc cagaggctac tacggtatgg acgtctgggg ccaagggacc      360
acggtcaccg tctcctca                                                   378

<210> SEQ ID NO 18
<211> LENGTH: 126
<212> TYPE: PRT
<213> ORGANISM: Homo sapiens
<220> FEATURE:
<221> NAME/KEY: SITE
<222> LOCATION: (31)...(35)
<223> OTHER INFORMATION: CDR1
<220> FEATURE:
<221> NAME/KEY: SITE
<222> LOCATION: (50)...(66)
<223> OTHER INFORMATION: CDR2
<220> FEATURE:
<221> NAME/KEY: SITE
<222> LOCATION: (99)...(115)
<223> OTHER INFORMATION: CDR3

<400> SEQUENCE: 18

```
Gln Val Gln Val Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Ile His Trp Val Arg Gln Ala Pro Gly Gln Gly Leu Glu Trp Met
             35                  40                  45

Gly Trp Ile Asn Pro Asp Ser Gly Gly Thr Asn Tyr Ala Gln Lys Phe
         50                  55                  60

Gln Gly Arg Val Thr Met Thr Arg Asp Thr Ser Ile Ser Thr Ala Tyr
```

```
                65                  70                  75                  80
Met Val Leu Asn Arg Leu Arg Ser Asp Asp Thr Ala Val Tyr Tyr Cys
                        85                  90                  95

Ala Lys Gly Gly Ile Asn Met Ile Val Val Ala Arg Gly Tyr Tyr Gly
                100                 105                 110

Met Asp Val Trp Gly Gln Gly Thr Thr Val Thr Val Ser Ser
        115                 120                 125

<210> SEQ ID NO 19
<211> LENGTH: 15
<212> TYPE: DNA
<213> ORGANISM: Homo sapiens

<400> SEQUENCE: 19
ggctactata tacac                                                             15

<210> SEQ ID NO 20
<211> LENGTH: 5
<212> TYPE: PRT
<213> ORGANISM: Homo sapiens

<400> SEQUENCE: 20

Gly Tyr Tyr Ile His
 1               5

<210> SEQ ID NO 21
<211> LENGTH: 51
<212> TYPE: DNA
<213> ORGANISM: Homo sapiens

<400> SEQUENCE: 21
tggatcaacc ctgacagtgg tggcacaaac tatgcacaga gtttcaggg c                      51

<210> SEQ ID NO 22
<211> LENGTH: 17
<212> TYPE: PRT
<213> ORGANISM: Homo sapiens

<400> SEQUENCE: 22

Trp Ile Asn Pro Asp Ser Gly Gly Thr Asn Tyr Ala Gln Lys Phe Gln
 1               5                  10                  15

Gly

<210> SEQ ID NO 23
<211> LENGTH: 51
<212> TYPE: DNA
<213> ORGANISM: Homo sapiens

<400> SEQUENCE: 23 gggggatca atatgatagt agtggccaga ggctactacg gtatggacgt c                      51

<210> SEQ ID NO 24
<211> LENGTH: 17
<212> TYPE: PRT
<213> ORGANISM: Homo sapiens

<400> SEQUENCE: 24

Gly Gly Ile Asn Met Ile Val Val Ala Arg Gly Tyr Tyr Gly Met Asp
 1               5                  10                  15

Val
```

<210> SEQ ID NO 25
<211> LENGTH: 321
<212> TYPE: DNA
<213> ORGANISM: Homo sapiens

<400> SEQUENCE: 25
gacatccaga tgacccagtc tccatcctcc ctgtctgcat ctgtaggaga cagagtcacc      60
atcacttgcc ggacaagtca gagcattggt aggtacttaa attggtatca gcagaaacca     120
gggaaagccc ctaaactcct catctatgga gcatccagtt tacaaagtgg ggtcccatca     180
agattcagtg gcagtggatc tgggacagaa ttcactttca tcatcagcag cctgcaacct     240
gaagattttg caacttacta ctgtcagcag agtttcaggg tccctatcac cttcggccaa     300
gggacacgac tggagattaa a                                                321

<210> SEQ ID NO 26
<211> LENGTH: 107
<212> TYPE: PRT
<213> ORGANISM: Homo sapiens
<220> FEATURE:
<221> NAME/KEY: SITE
<222> LOCATION: (24)...(34)
<223> OTHER INFORMATION: CDR1
<220> FEATURE:
<221> NAME/KEY: SITE
<222> LOCATION: (50)...(56)
<223> OTHER INFORMATION: CDR2
<220> FEATURE:
<221> NAME/KEY: SITE
<222> LOCATION: (89)...(97)
<223> OTHER INFORMATION: CDR3

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Phe Ile Ile Ser Ser Leu Gln Pro
65                  70                  75                  80

Glu Asp Phe Ala Thr Tyr Tyr Cys Gln Gln Ser Phe Arg Val Pro Ile
                85                  90                  95

Thr Phe Gly Gln Gly Thr Arg Leu Glu Ile Lys
            100                 105

<210> SEQ ID NO 27
<211> LENGTH: 33
<212> TYPE: DNA
<213> ORGANISM: Homo sapiens

<400> SEQUENCE: 27
cggacaagtc agagcattgg taggtactta aat                                    33

<210> SEQ ID NO 28
<211> LENGTH: 11
<212> TYPE: PRT
<213> ORGANISM: Homo sapiens

<400> SEQUENCE: 28

Arg Thr Ser Gln Ser Ile Gly Arg Tyr Leu Asn

<210> SEQ ID NO 29
<211> LENGTH: 21
<212> TYPE: DNA
<213> ORGANISM: Homo sapiens

<400> SEQUENCE: 29
ggagcatcca gtttacaaag t                                                21

<210> SEQ ID NO 30
<211> LENGTH: 7
<212> TYPE: PRT
<213> ORGANISM: Homo sapiens

<400> SEQUENCE: 30

Gly Ala Ser Ser Leu Gln Ser
1               5

<210> SEQ ID NO 31
<211> LENGTH: 27
<212> TYPE: DNA
<213> ORGANISM: Homo sapiens

<400> SEQUENCE: 31
cagcagagtt tcagggtccc tatcacc                                          27

<210> SEQ ID NO 32
<211> LENGTH: 9
<212> TYPE: PRT
<213> ORGANISM: Homo sapiens

<400> SEQUENCE: 32

Gln Gln Ser Phe Arg Val Pro Ile Thr
1               5

<210> SEQ ID NO 33
<211> LENGTH: 1670
<212> TYPE: DNA
<213> ORGANISM: Homo sapiens
<220> FEATURE:
<221> NAME/KEY: CDS
<222> LOCATION: (69)...(1175)

<400> SEQUENCE: 33
ccaaccacaa gcaccaaagc agaggggcag gcagcacacc acccagcagc cagagcacca      60 gcccagcc atg gtc ctt gag gtg agt gac cac caa gtg cta aat gac gcc     110
         Met Val Leu Glu Val Ser Asp His Gln Val Leu Asn Asp Ala
           1               5                  10 gag gtt gcc gcc ctc ctg gag aac ttc agc tct tcc tat gac tat gga     158
Glu Val Ala Ala Leu Leu Glu Asn Phe Ser Ser Ser Tyr Asp Tyr Gly
 15                  20                  25                  30 gaa aac gag agt gac tcg tgc tgt acc tcc ccg ccc tgc cca cag gac     206
Glu Asn Glu Ser Asp Ser Cys Cys Thr Ser Pro Pro Cys Pro Gln Asp
                 35                  40                  45 ttc agc ctg aac ttc gac cgg gcc ttc ctg cca gcc ctc tac agc ctc     254
Phe Ser Leu Asn Phe Asp Arg Ala Phe Leu Pro Ala Leu Tyr Ser Leu
             50                  55                  60 ctc ttt ctg ctg ggg ctg ctg ggc aac ggc gcg gtg gca gcc gtg ctg     302
Leu Phe Leu Leu Gly Leu Leu Gly Asn Gly Ala Val Ala Ala Val Leu
         65                  70                  75 ctg agc cgg cgg aca gcc ctg agc agc acc gac acc ttc ctg ctc cac     350
Leu Ser Arg Arg Thr Ala Leu Ser Ser Thr Asp Thr Phe Leu Leu His
     80                  85                  90

-continued

```
              80                  85                  90
cta gct gta gca gac acg ctg ctg gtg ctg aca ctg ccg ctc tgg gca      398
Leu Ala Val Ala Asp Thr Leu Leu Val Leu Thr Leu Pro Leu Trp Ala
 95                 100                 105                 110 gtg gac gct gcc gtc cag tgg gtc ttt ggc tct ggc ctc tgc aaa gtg      446
Val Asp Ala Ala Val Gln Trp Val Phe Gly Ser Gly Leu Cys Lys Val
                    115                 120                 125 gca ggt gcc ctc ttc aac atc aac ttc tac gca gga gcc ctc ctg ctg      494
Ala Gly Ala Leu Phe Asn Ile Asn Phe Tyr Ala Gly Ala Leu Leu Leu
        130                 135                 140 gcc tgc atc agc ttt gac cgc tac ctg aac ata gtt cat gcc acc cag      542
Ala Cys Ile Ser Phe Asp Arg Tyr Leu Asn Ile Val His Ala Thr Gln
145                 150                 155 ctc tac cgc cgg ggg ccc ccg gcc cgc gtg acc ctc acc tgc ctg gct      590
Leu Tyr Arg Arg Gly Pro Pro Ala Arg Val Thr Leu Thr Cys Leu Ala
        160                 165                 170 gtc tgg ggg ctc tgc ctg ctt ttc gcc ctc cca gac ttc atc ttc ctg      638
Val Trp Gly Leu Cys Leu Leu Phe Ala Leu Pro Asp Phe Ile Phe Leu
175                 180                 185                 190 tcg gcc cac cac gac gag cgc ctc aac gcc acc cac tgc caa tac aac      686
Ser Ala His His Asp Glu Arg Leu Asn Ala Thr His Cys Gln Tyr Asn
                    195                 200                 205 ttc cca cag gtg ggc cgc acg gct ctg cgg gtg ctg cag ctg gtg gct      734
Phe Pro Gln Val Gly Arg Thr Ala Leu Arg Val Leu Gln Leu Val Ala
        210                 215                 220 ggc ttt ctg ctg ccc ctg ctg gtc atg gcc tac tgc tat gcc cac atc      782
Gly Phe Leu Leu Pro Leu Leu Val Met Ala Tyr Cys Tyr Ala His Ile
225                 230                 235 ctg gcc gtg ctg ctg gtt tcc agg ggc cag cgg cgc ctg cgg gcc atg      830
Leu Ala Val Leu Leu Val Ser Arg Gly Gln Arg Arg Leu Arg Ala Met
240                 245                 250 cgg ctg gtg gtg gtg gtc gtg gtg gcc ttt gcc ctc tgc tgg acc ccc      878
Arg Leu Val Val Val Val Val Val Ala Phe Ala Leu Cys Trp Thr Pro
255                 260                 265                 270 tat cac ctg gtg gtg ctg gtg gac atc ctc atg gac ctg ggc gct ttg      926
Tyr His Leu Val Val Leu Val Asp Ile Leu Met Asp Leu Gly Ala Leu
                    275                 280                 285 gcc cgc aac tgt ggc cga gaa agc agg gta gac gtg gcc aag tcg gtc      974
Ala Arg Asn Cys Gly Arg Glu Ser Arg Val Asp Val Ala Lys Ser Val
        290                 295                 300 acc tca ggc ctg ggc tac atg cac tgc tgc ctc aac ccg ctc tc tat     1022
Thr Ser Gly Leu Gly Tyr Met His Cys Cys Leu Asn Pro Leu Leu Tyr
305                 310                 315 gcc ttt gta ggg gtc aag ttc cgg gag cgg atg tgg atg ctg ctc ttg     1070
Ala Phe Val Gly Val Lys Phe Arg Glu Arg Met Trp Met Leu Leu Leu
320                 325                 330 cgc ctg ggc tgc ccc aac cag aga ggg ctc cag agg cag cca tcg tct     1118
Arg Leu Gly Cys Pro Asn Gln Arg Gly Leu Gln Arg Gln Pro Ser Ser
335                 340                 345                 350 tcc cgc cgg gat tca tcc tgg tct gag acc tca gag gcc tcc tac tcg     1166
Ser Arg Arg Asp Ser Ser Trp Ser Glu Thr Ser Glu Ala Ser Tyr Ser
                    355                 360                 365 ggc ttg tga ggccggaatc cgggctcccc tttcgccac agtctgactt              1215
Gly Leu * ccccgcattc caggctcctc cctccctctg ccggctctgg ctctcccaa tatcctcgct    1275 cccgggactc actggcagcc ccagcaccac caggtctccc gggaagccac cctcccagct   1335 tgaggactg caccattgct gctccttagc tgccaagccc catcctgccg cccgaggtgg    1395
```

-continued

```
tgcctggag ccccactgcc cttctcattt ggaaactaaa acttcatctt ccccaagtgc    1455 gggagtaca aggcatggcg tagagggtgc tgccccatga agccacagcc caggcctcca    1515 ctcagcagt gactgtggcc atggtcccca agacctctat atttgctctt ttattttat    1575 tctaaaatc ctgcttaaaa cttttcaata aacaagatcg tcaggacctt tttttttttt    1635 tttttttt tttttttttt tttttttttt ttttt                               1670
```

<210> SEQ ID NO 34
<211> LENGTH: 368
<212> TYPE: PRT
<213> ORGANISM: Homo sapiens

<400> SEQUENCE: 34

```
Met Val Leu Glu Val Ser Asp His Gln Val Leu Asn Asp Ala Glu Val
 1               5                  10                  15

Ala Ala Leu Leu Glu Asn Phe Ser Ser Tyr Asp Tyr Gly Glu Asn
             20                  25                  30

Glu Ser Asp Ser Cys Cys Thr Ser Pro Pro Cys Pro Gln Asp Phe Ser
         35                  40                  45

Leu Asn Phe Asp Arg Ala Phe Leu Pro Ala Leu Tyr Ser Leu Leu Phe
     50                  55                  60

Leu Leu Gly Leu Gly Asn Gly Ala Val Ala Val Leu Leu Ser
 65                  70                  75                  80

Arg Arg Thr Ala Leu Ser Ser Thr Asp Thr Phe Leu Leu His Leu Ala
                 85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
            260                 265                 270

Leu Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
```

```
                           325                 330                 335
Gly Cys Pro Asn Gln Arg Gly Leu Gln Arg Gln Pro Ser Ser Ser Arg
            340                 345                 350
Arg Asp Ser Ser Trp Ser Glu Thr Ser Glu Ala Ser Tyr Ser Gly Leu
        355                 360                 365

<210> SEQ ID NO 35
<211> LENGTH: 98
<212> TYPE: PRT
<213> ORGANISM: Homo sapiens

<400> SEQUENCE: 35

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Met Ser Lys Arg
                85                  90                  95

Ser Pro

<210> SEQ ID NO 36
<211> LENGTH: 125
<212> TYPE: PRT
<213> ORGANISM: Homo sapiens

<400> SEQUENCE: 36

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
                100                 105                 110

Val Arg Lys Ser Gln Arg Ser Arg Gln Lys Lys Thr Thr
        115                 120                 125

<210> SEQ ID NO 37
<211> LENGTH: 94
<212> TYPE: PRT
<213> ORGANISM: Homo sapiens

<400> SEQUENCE: 37

Met Ser Val Lys Gly Met Ala Ile Ala Leu Ala Val Ile Leu Cys Ala
1               5                   10                  15
```

-continued

```
Thr Val Val Gln Gly Phe Pro Met Phe Lys Arg Gly Arg Cys Leu Cys
             20                  25                  30

Ile Gly Pro Gly Val Lys Ala Val Lys Val Ala Asp Ile Glu Lys Ala
         35                  40                  45

Ser Ile Met Tyr Pro Ser Asn Asn Cys Asp Lys Ile Glu Val Ile Ile
     50                  55                  60

Thr Leu Lys Glu Asn Lys Gly Gln Arg Cys Leu Asn Pro Lys Ser Lys
 65                  70                  75                  80

Gln Ala Arg Leu Ile Ile Lys Lys Val Glu Arg Lys Asn Phe
                 85                  90
```

<210> SEQ ID NO 38
<211> LENGTH: 49
<212> TYPE: DNA
<213> ORGANISM: Artificial Sequence
<220> FEATURE:
<223> OTHER INFORMATION: primer

<400> SEQUENCE: 38
ttacccaatt gtgtcctgtc ccaggtgcag gtggtgcagt ctggggctg            49

<210> SEQ ID NO 39
<211> LENGTH: 50
<212> TYPE: DNA
<213> ORGANISM: Artificial Sequence
<220> FEATURE:
<223> OTHER INFORMATION: primer

<400> SEQUENCE: 39
tggaggctga gctgacggtg accgtggtcc cttggcccca gacgtccata           50

<210> SEQ ID NO 40
<211> LENGTH: 51
<212> TYPE: DNA
<213> ORGANISM: Artificial Sequence
<220> FEATURE:
<223> OTHER INFORMATION: primer

<400> SEQUENCE: 40
ttcccagggt cccgttccga catccagatg acccagtctc catcctccct g         51

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
agccaccgta cgcttaatct ccagtcgtgt cccttg                          36

<210> SEQ ID NO 42
<211> LENGTH: 47
<212> TYPE: DNA
<213> ORGANISM: Artificial Sequence
<220> FEATURE:
<223> OTHER INFORMATION: primer

<400> SEQUENCE: 42
ctgaaccttg atgggactcc actttgcaaa ctggatgcgc catagat               47

<210> SEQ ID NO 43
<211> LENGTH: 49
<212> TYPE: DNA

-continued

```
<213> ORGANISM: Artificial Sequence
<220> FEATURE:
<223> OTHER INFORMATION: primer

<400> SEQUENCE: 43
tccagtttgc aaagtggagt cccatcaagg ttcagtggca gtggatctg                    49

<210> SEQ ID NO 44
<211> LENGTH: 83
<212> TYPE: DNA
<213> ORGANISM: Artificial Sequence
<220> FEATURE:
<223> OTHER INFORMATION: primer

<400> SEQUENCE: 44
agccaccgta cgcttaatct ccagtcgtgt cccttggccg aaactgatag ggactctgaa        60
actctgttga cagtagtaag ttg                                                83
```